United States Patent [19]

Logan et al.

[11] 4,226,148
[45] Oct. 7, 1980

[54] DEVICE FOR TRANSLATING AND ROTATING A CUTTING PLATEN WITH RESPECT TO A RECIPROCAL CUTTER

[75] Inventors: David J. Logan, Glastonbury; Robert J. Pavone, South Windsor, both of Conn.

[73] Assignee: Gulf & Western Corporation, New York, N.Y.

[21] Appl. No.: 902,263

[22] Filed: May 2, 1978

[51] Int. Cl.³ .................... A24C 1/00; A24C 1/04; B26D 5/30
[52] U.S. Cl. ...................................... 83/71; 83/451; 83/925 R; 83/367; 131/33; 131/21 R; 131/122
[58] Field of Search ................ 83/70, 71, 451, 925 R, 83/367; 131/21 R, 28 R, 33, 36, 122

[56] References Cited
U.S. PATENT DOCUMENTS

| 2,866,506 | 12/1958 | Hierath et al. | 83/71 |
| 3,199,514 | 8/1965 | Petri et al. | 131/33 |
| 3,232,142 | 2/1966 | Oeckl | 83/71 |
| 3,691,887 | 9/1972 | Roch | 83/71 |
| 3,908,723 | 9/1975 | Hill | 83/71 |
| 4,148,238 | 4/1979 | Mortensen et al. | 83/451 |

Primary Examiner—Donald R. Schran
Attorney, Agent, or Firm—Meyer, Tilberry & Body

[57] ABSTRACT

A device for cutting a piece of a flat workpiece at a selected location identifiable by two or more binary coded numbers which device includes a cutter, a cutting platen having an upper workpiece supporting surface and a lower portion, a plurality of upstanding, shiftable members, a guiding arrangement on the platen adjacent the lower portion for loosely receiving the members, an arrangement for moving the members in accordance with the coded numbers and a structure for forcing the cutter against the cutting surface. In accordance with another aspect, the shiftable members are movable by binary fluid motors each including a series of axially aligned fluid actuating units having strokes corresponding to binary numbers and an arrangement for actuating certain of these units in the fluid motor to move the shiftable members in accordance with the extended condition of the binary motors.

14 Claims, 49 Drawing Figures

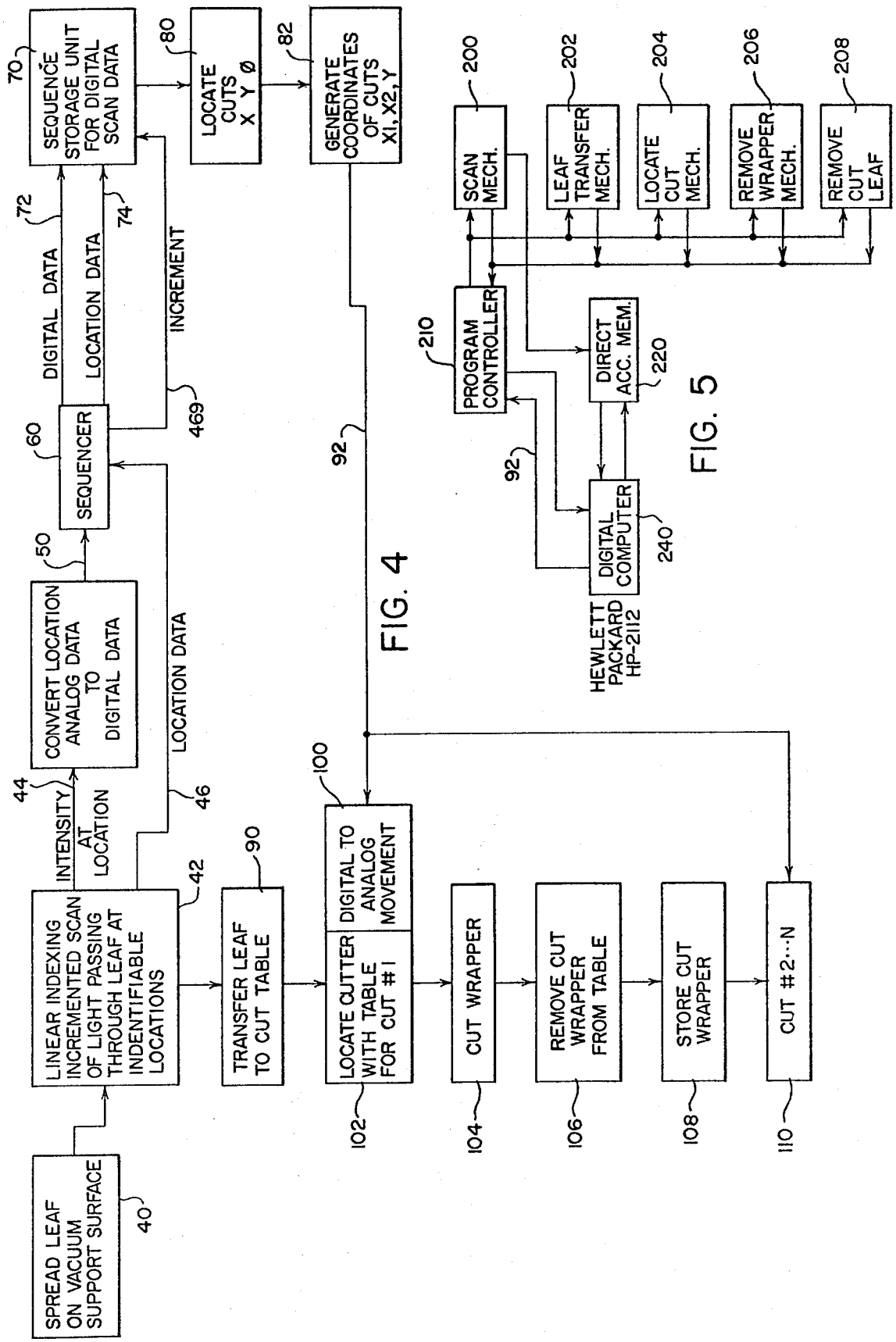

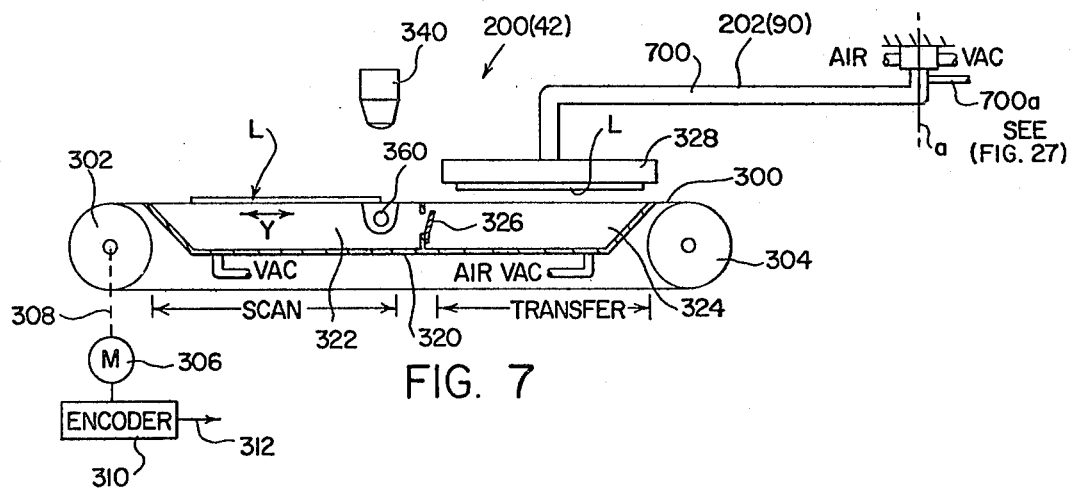
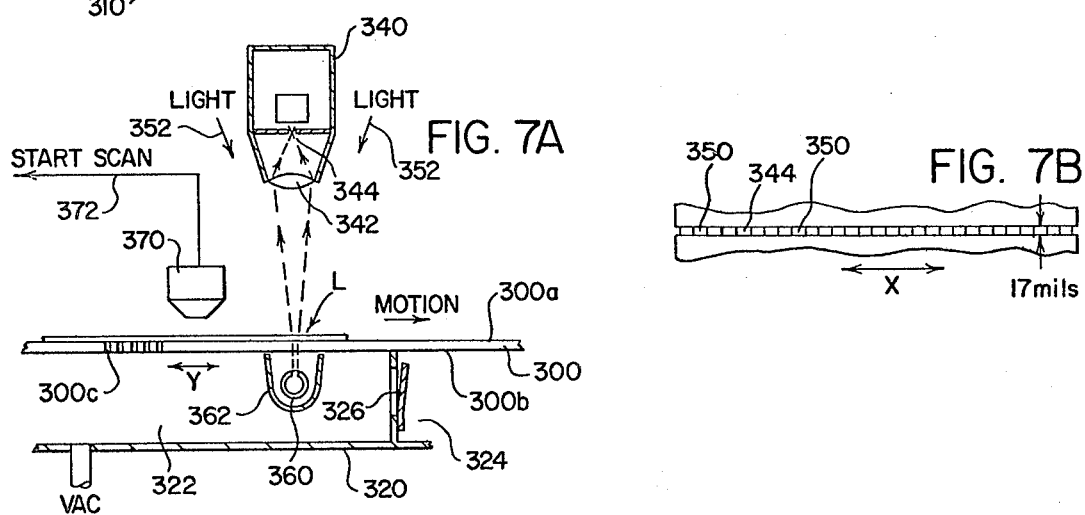
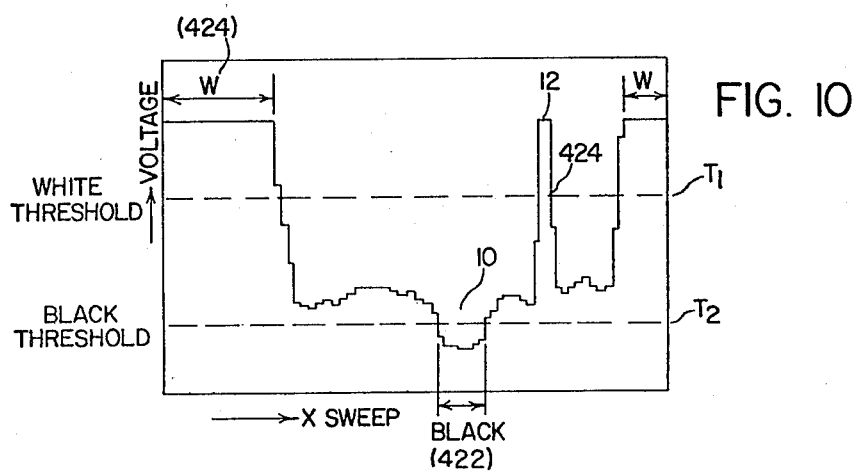

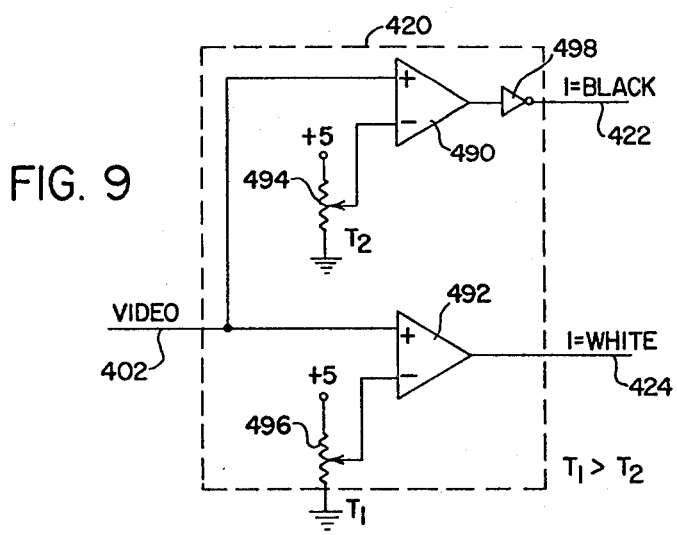
FIG. 9
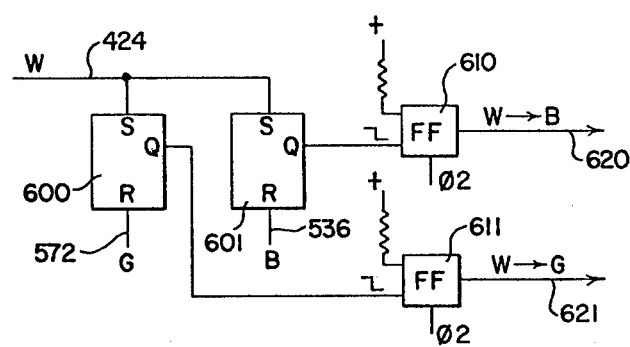
FIG. 14
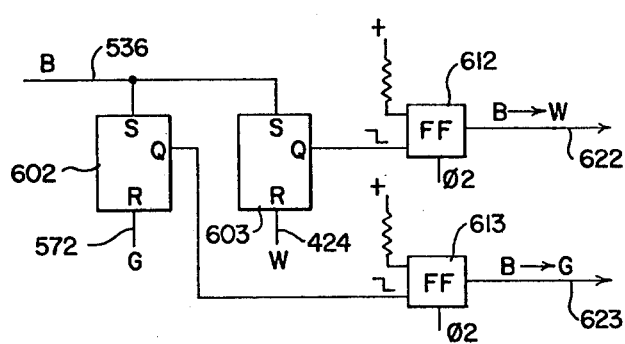
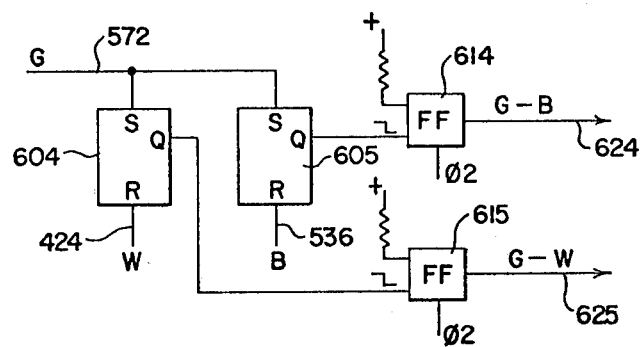

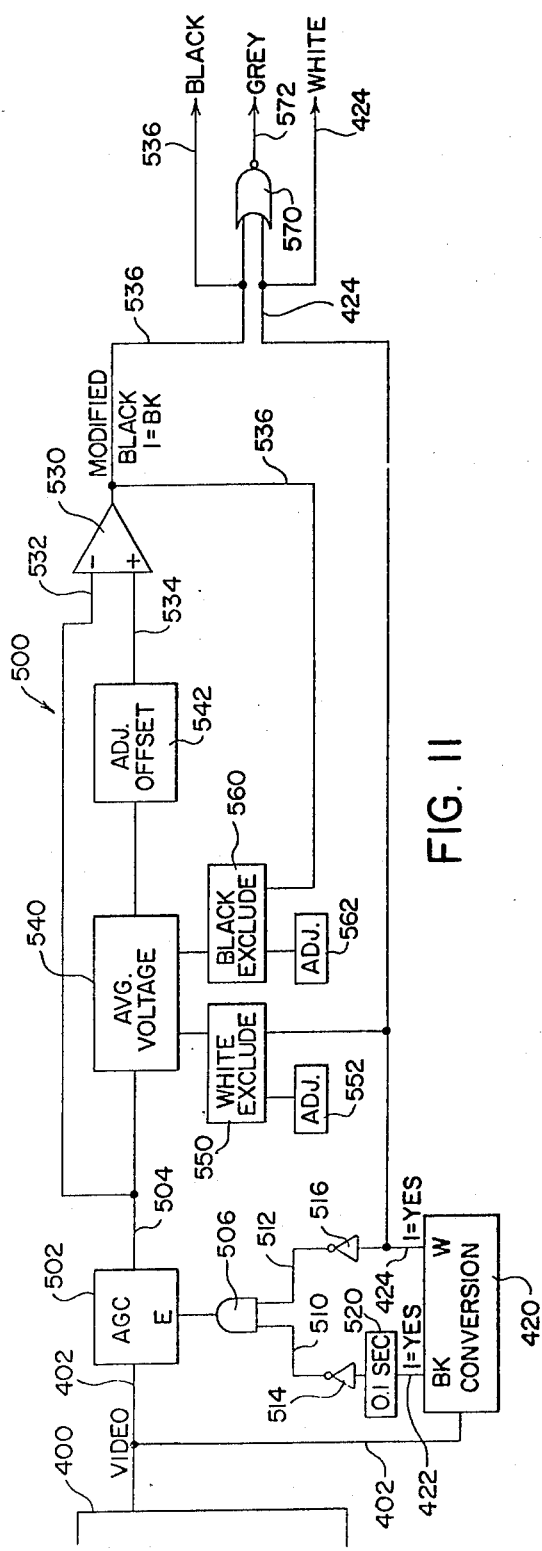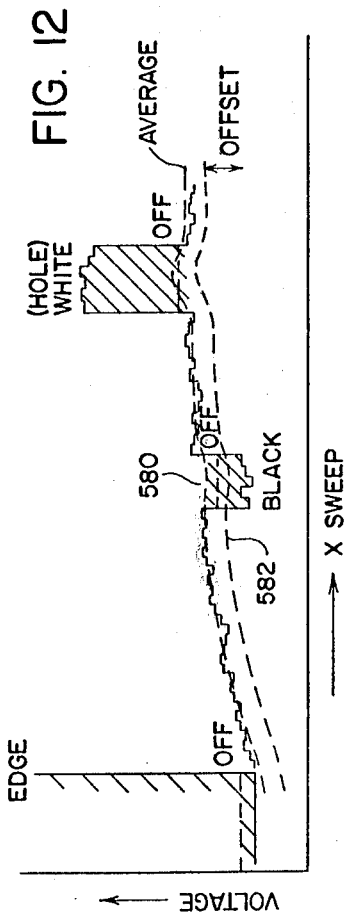

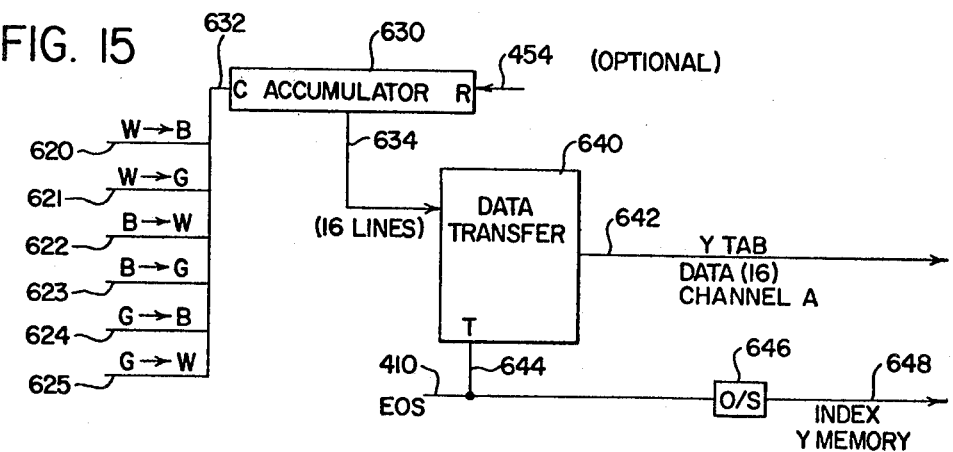
FIG. 15
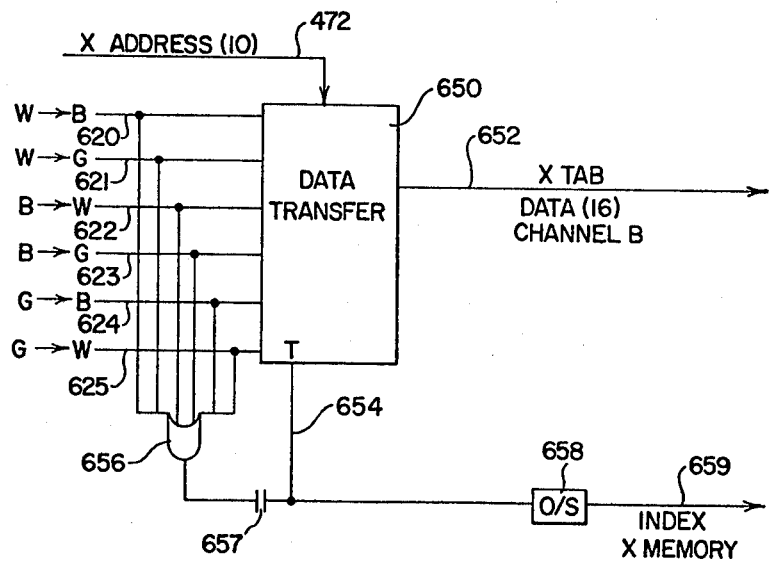
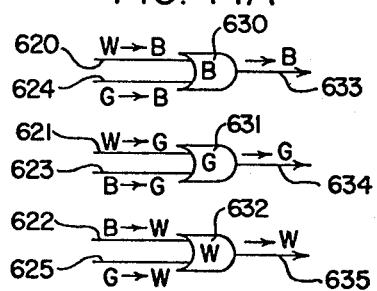
FIG. 14A

| MEMORY LOCATION | X TAB  662 |
|---|---|
| — 0000 | → G ADD |
| — 0001 | → W ADD |
| — 0010 | → G ADD |
| — 0011 | → W ADD |
| — 0100 | → G ADD |
| — 0101 | → B ADD |
| — 0110 | → G ADD |
| — 0111 | → W ADD |
| — 1000 | → G ADD |
| — 1001 | → W ADD |
| — 1010 | → G ADD |
| — 1011 | → B ADD |
| — 1100 | → G ADD |
| — 1101 | → B ADD |
| — 1110 | → G ADD |
| 1111 | → W ADD |
| " | |

FIG. 20

| LINE | Y TAB  660 | |
|---|---|---|
| 1 | 0 | |
| 2 | 0 | |
| 3 | 2 | →G →W |
| 4 | 4 | →G →W |
| 5 | 8 | →G →B →G →W |
| 6 | 16 | →G →W →G →B →G →B →G →W |
| 7 | 22 | " |
| 8 | 30 | |
| 9 | 38 | |
| 10 | 50 | |
| 11 | 58 | |
| 506 | 830 | |
| 507 | 832 | |
| 508 | 834 | |
| 509 | 834 | |
| 510 | 834 | |
| 511 | 834 | |
| 512 | 834 | |

FIG. 19

HOLE (WHITE DOMAIN)

PROGRAM
(OUTLINE)

(1) HAS X TAB AND Y TAB BEEN STORED IN MEMORY (DIRECT ACCESS)?
(2) LOOK FOR FIRST WHITE TO GRAY TRANSITION AND LAST GRAY TO WHITE TRANSITION.
(3) STORE TRANSITIONS
(4) REPEAT (2) AND (3) FOR EACH 40th Y LINE
(5) CALCULATE LEAF EDGE VECTORS BETWEEN ADJACENT TRANSITIONS.
(6) STORE LEAF EDGE VECTORS
(7) LOOK FOR TRANSITIONS TO AND FROM WHITE IN EACH Y LINE
(8) STORE DOMAIN OF WHITE REGION (MIN X, MIN Y; MAX X, MAX Y)
(9) STORE HOLE DOMAINS
(10) LOOK FOR BLACK TRANSITIONS IN EACH 5th Y LINE
(11) CONSTRUCT STEM LINE BASED UPON REPEATED BLACK TRANSITIONS AT SAME POSITIONS IN ADJACENT 5th Y LINES.
(12) CONSTRUCT SAFE LINES ON EACH SIDE OF STEM BASED UPON CONSTRUCTED STEM AND EXCLUDING ALL STEM BLACK
(13) ARITHMETIC PLACEMENT OF CUT OUTLINE IN VECTOR FORM ADJACENT TO CONSTRUCTED SAFE LINE AT TIP OF LEAF
(14) CHECK INTERSECTION OF LEAF EDGE VECTORS
(15) IF NOT OK, SHIFT CUT OUTLINE ALONG SAFE LINE A GIVEN AMOUNT AND REPEAT UNTIL (14) CHECKS OK.
(16) IF OK REGARDING LEAF OUTLINE, CHECK EXISTENCE OF HOLE COORDINATES WITHIN CUT OUTLINE. (HOLES OK IF LESS THAN SELECTED SIZE IN X AND Y DIRECTIONS)
(17) IF NOT OK REGARDING HOLE LOCATIONS, SHIFT OUTLINE ALONG SAFE LINE A SELECTED DISTANCE AND RECHECK (14),(16)
(18) IF OK REGARDING LEAF OUTLINE AND HOLE LOCATIONS, CHECK BLACK DATA AND EXISTENCE OF ANY HOLE IN SELECTED AREAS OF CUT PROFILE
(19) IF NOT OK, SHIFT AND CHECK (14),(16),(18)
(20) IF REACH OPPOSITE LEAF OUTLINE VECTOR, SHIFT Y DIRECTION CONSTRUCT NEW SAFE LINE AND REPEAT STEPS (13),(14),(16),(18)
(21) REPEAT UNTIL ALL CHECKS OK OR EXHAUST LEAF HALF, WHICHEVER COMES FIRST
(22) WHEN ALL OK, NOTE X1, X2 AND Y COORDINATES FOR SELECTED CUT OUTLINE POSITION
(23) STORE CUT COORDINATES
(24) ADD CUT OUTLINE VECTORS AT X1, X2 AND Y COORDINATES TO LEAF OUTLINE VECTORS
(25) REPEAT FOR NEXT CUT FROM (13) OR CUTS ON SECOND LEAF HALF
(26) REPEAT FOR SECOND LEAF HALF FROM STEP (12)
(27) CREATE READY SIGNAL
(28) DOES PROGRAMMABLE CONTROLLER WANT DATA?
(29) IF NO, WAIT FOR YES
(30) IF YES, TRANSFER DATA TO PROGRAMMABLE CONTROLLER

FIG. 26

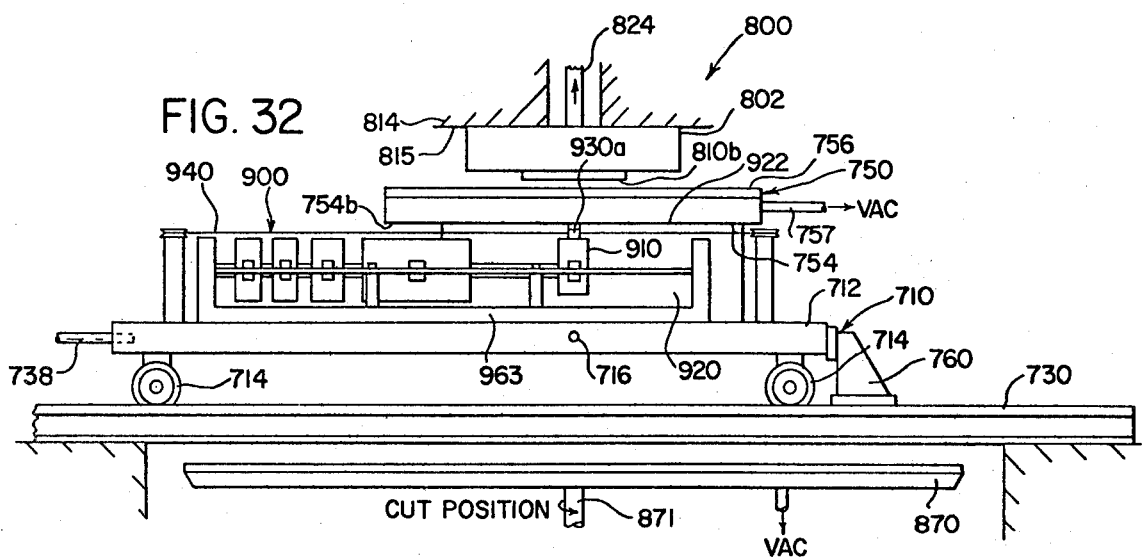
FIG. 32
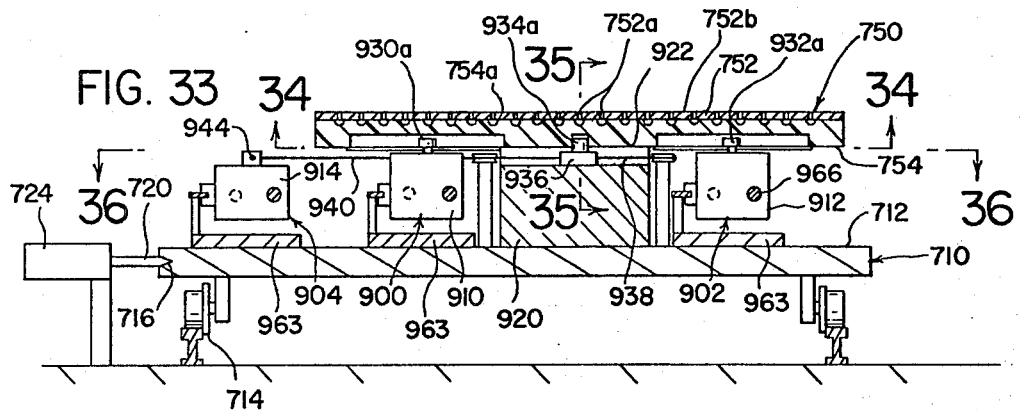
FIG. 33
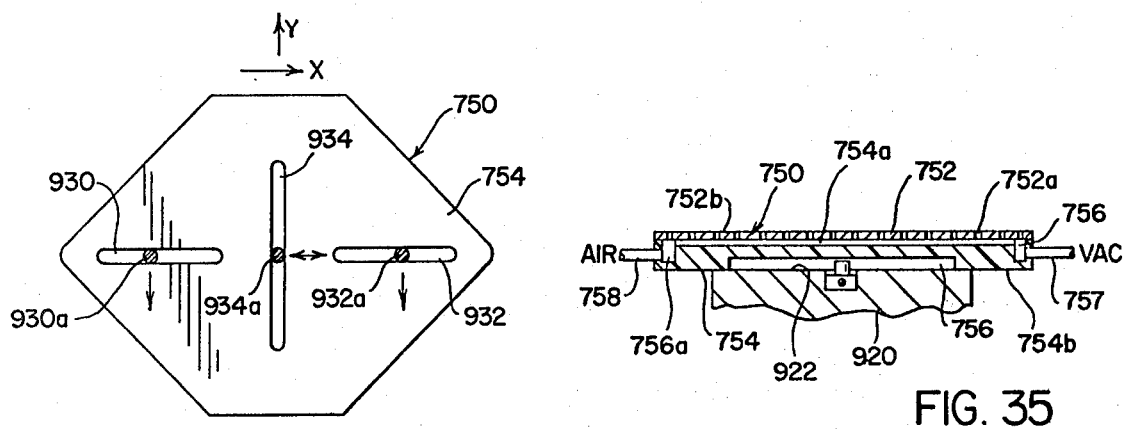
FIG. 34
FIG. 35

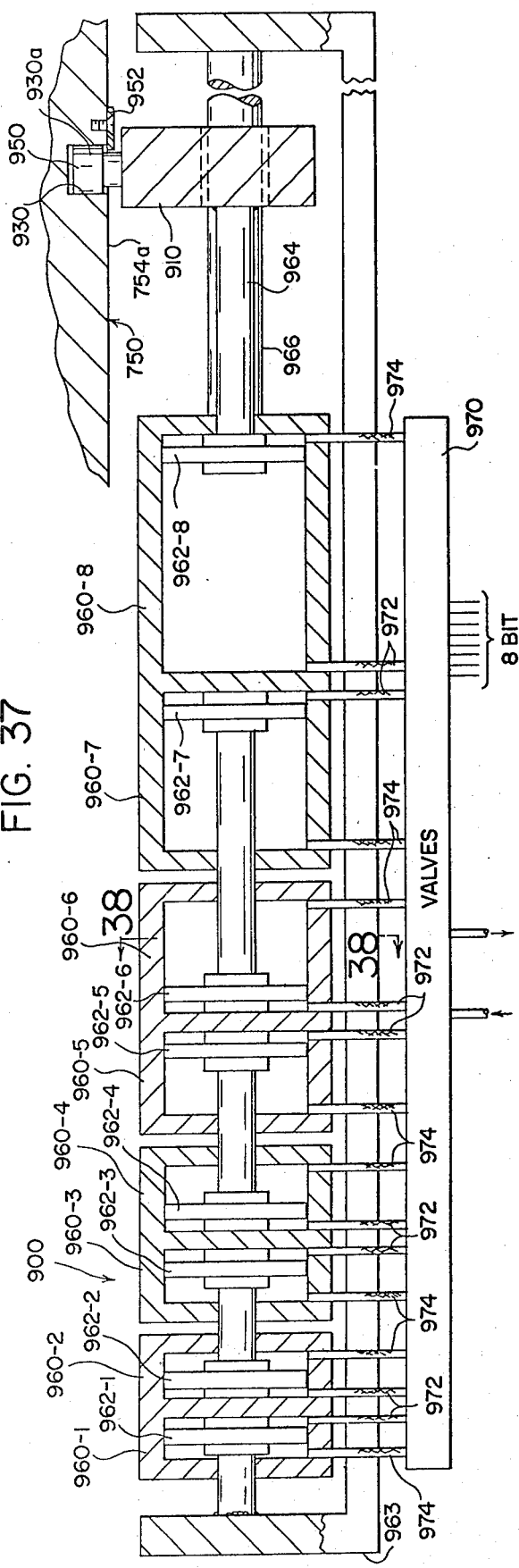
FIG. 37
FIG. 38
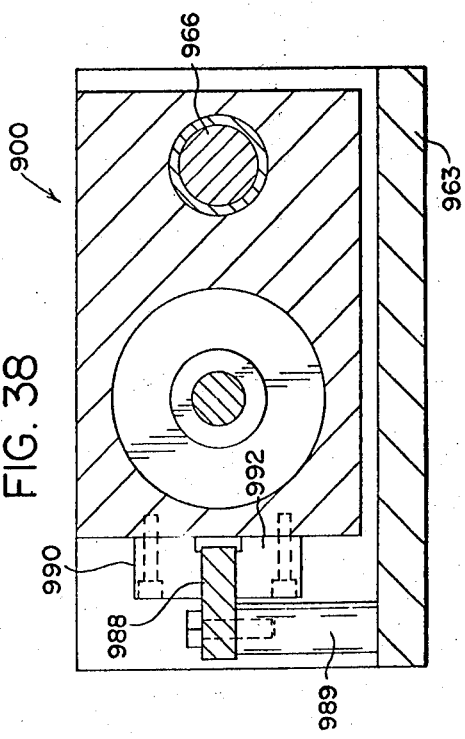
FIG. 39

DEVICE FOR TRANSLATING AND ROTATING A CUTTING PLATEN WITH RESPECT TO A RECIPROCAL CUTTER

The present invention relates to the art of cutting sheet material with a reciprocal cutter and more particularly to a device for translating and rotating a cutting platen carrying the material with respect to a reciprocal cutter. This invention is particularly applicable for use in a machine wherein cigar wrappers are cut from a natural tobacco leaf and will be described with particular reference thereto; however, it should be appreciated that the invention has broader applications and may be used with other sheet cutting devices.

CROSS REFERENCE

This application claims subject matter from a companion, copending application Ser. No. 884,849, filed Mar. 9, 1978, owned by a common assignee.

BACKGROUND OF THE INVENTION

In the production of cigars, a core is usually provided. In practice, the core is formed either of small tobacco pieces or whole tobacco leaves bunched in a longitudinal direction. These cores are usually wrapped with a binder and then spirally wrapped by an elongated sheet, known as a "wrapper". The cigar wrapper is formed by cutting a given profile from a tobacco sheet product. In some instances, a wrapper is cut from a synthetic tobacco sheet. However, it is desirable to provide a natural tobacco leaf as the outer cigar wrapper to present an appealing appearance which facilitates marketing of the finished cigar. It is essential for a quality cigar that a natural tobacco leaf be used for the outer wrapper and that the finished cigar have no noticeable defect, such as a hole, a color variation, an edge portion of the leaf, or a stem. Indeed, certain unduly noticeable heavy veins should not be incorporated into a wrapper for a quality cigar. All of these concepts in wrapper selection are essential in the marketing of a cigar in the very competitive cigar industry. The wrapper is important in determining the overall visual concept that a purchaser forms regarding the quality of the cigar. Consequently, the wrapper must have an appearance that imparts an impression of quality to the resulting cigar.

As is well knon in the cigar industry, the wrapper, which is helically disposed in overlapping fashion around the cigar, must also have a smooth outer appearance which is somewhat difficult to obtain since the shape of the cigar often varies along its length. For that reason, the wrapper must be cut in a complex shape and must be accurately spiraled around the cigar core and/or binder to produce the desired smooth outer appearance. This requirement, combined with the demand for a cigar wrapper with no surface defects, has made one of the more critical aspects of cigar making the system by which the cigar wrapper is cut from a natural tobacco leaf. This system is made quite complex by the fact that each natural tobacco leaf has differet surface variations which must be excluded from a wrapper.

Due to the extreme criticality in producing quality cigar wrappers for use in cigar manufacturing, the wrappers are generally cut by a manual orienting procedure that has not changed substantially over the years. The process requires a skilled operator who manually orients a half of a leaf formed by removing the center stem. This leaf portion or half is examined for holes, coarse veins, or other visible imperfections on one surface. After this inspection, the leaf portion is usually spread onto a cutting surface including a cutting die surrounded by perforated surfaces through which vacuum can be applied to the spread leaf. The leaf is manually positioned over the cutting die to insure that the outline of the die, which has the shape of the cigar wrapper, does not include an edge portion or any other visible surface imperfection in the natural tobacco leaf. After this placement has been made, the vacuum is applied to hold the leaf in place on the cutting surface. A roller is forced over the leaf and cuts out a leaf portion determined by the profile of the cutter over which the leaf was positioned. After a first cut has been made, the vacuum is released, the wrapper is removed and the cut tobacco portion is again oriented by the operator for a second cut from the leaf half, if a second cut is possible without including any surface imperfection. The wrapper has an elongated shape and the leaf veins must have a predetermined diagonal orientation in the wrapper. Consequently, the general disposition of the wrapper cut must be generally parallel to the original stem of the natural tobacco leaf within a few degrees, such as 10°–15°. In this manner, the veins, which are found on the leaf, will have the proper pattern when the wrapper is spirally wound around the core and/or binder to form a finished cigar. This process of manually orienting and then cutting is continued until no other wrapper can be cut from a leaf half. At this time, the leaf is removed from the cutting station for use in other tobacco products or discarded. Other procedures are used in the tobacco industry for producing the cigar wrappers. This particular description is representative in that each of the procedures involves manual manipulation of a leaf or a leaf half into a particular position wherein a cut is made in the natural tobacco leaf so as to avoid surface imperfections. In all instances, an operator, who must be skilled and highly trained, is required for the production of a quality wrapper produced from a natural tobacco leaf. In practice, the cost of producing the quality wrapper is a relatively high proportion of the cigar manufacturing costs in that the remainder of the cigar making process is generally mechanized and can be accomplished at relatively high processing speeds.

In view of this, there is a substantial demand for an arrangement wherein the cigar wrapper can be cut from a tobacco leaf in a high speed operation involving no manual manipulation without sacrificing the high quality required for the production of such wrappers. The advantage to the cigar manufacturing process of avoiding, or reducing, the manual manipulation required in producing the cigar wrappers is well known in the industry.

Before the leaves are stacked for use by an operator, the heavy stem or mid-rib of each tobacco leaf is removed. Each resulting half of the leaf is then "booked" in a separate pile for use in the cutting operation. Since the veins in the leaf extend diagonally in different general directions with respect to the stem, one half of the leaf is used for one cigar making machine and the other half of the leaf is used for another cigar making machine. This prevents mixing of wrappers from both leaf halves so that the diagonal veins within the cigar wrapper are uniform for each run of cigars. If whole leaves were provided to the operator for manual orientation and cutting, the cut wrappers could have different vein patterns unless the operator exercised extreme care and attention. Such mixing of vein patterns would not be acceptable in the production of cigars. The wrappers must be consistent in the orientation of the vein angles. Consequently, not only have prior arrangements for cutting cigar wrappers required manual manipulation, but they have required stemming of the tobacco leaf and grouping the leaves in "booked" and matched halves for use in a particular tobacco wrapping machine. Stemming, booking and other controls have increased the cost of wrappers without increasing their quality. All of these disadvantages are known in the cigar industry and attempts have been made to correct one or more of the various disadvantages experienced in the previously used arrangements for producing cigar wrappers from natural tobacco leaves.

The most common approach to solving the problems in cutting wrappers has been to mechanize or increase the speed of the cutting operation and the wrapper transfer operation. Such a concept is shown in U.S. Pat. No. 3,591,044. This patent is incorporated herein by reference for background information only. Such an arrangement increases production by an operator, but it does not solve the basic problems involved in the efficient production of a wrapper from a natural tobacco leaf. Manual manipulation or orientation, stemming and booking of leaf halves are still required. This was the background situation presented when the present novel system was developed to cut cigar wrappers from natural tobacco leaves.

THE INVENTION

The present invention relates to a device for translating and rotating a cutting platen with respect to a reciprocal cutter of the type which is especially adapted for a machine or method of producing a cigar wrapper from a natural tobacco leaf by moving the platen to the desired cutting position and then reciprocating the cutter having the profile of the wrapper against the platen to cut the wrapper from the leaf.

In accordance with the present invention, there is provided a device for translating and rotating a cutting platen for a flat workpiece with respect to a reciprocable cutter, this device comprises first, second and third guide ways on the platen with the first and second guide ways extending generally in a first direction and a third guide way extending in a second direction at a known angle to the first direction. The first, second and third drive elements are slidably received in the first, second and third guide ways, respectively. Drive means for each of the drive elements are used to shift the drive elements in a direction generally transverse to the guide ways and control means are provided for shifting the drive means a selected distance in the drive direction to cause corresponding movement of the platen with respect to the cutter.

By using a device as defined above, the platen can be shifted in both a translation direction and a rotating direction without requiring rotary drive elements. Indeed, the use of the two first and second drive means can provide translation and rotation. The third means causes transverse movement of the cutting platen. By providing these combinations of elements, a platen can be moved into a variety of positions determined by the position of the drive elements. A binary signal can control the drive means to, in turn, control the drive elements for shifting the platen in any desired position controlled by binary input signals to the device as defined above.

In accordance with another aspect of the present invention, there is provided a device for cutting a piece from a flat workpiece at a location identified by two or more binary coded numbers. This device comprises a cutter, a cutting platen having an upper workpiece supporting surface and a lower portion, a plurality of upstanding, shiftable members, guide means on the platen adjacent the lower portion for loosely receiving the members, and means for moving the members in accordance with the coded numbers. The cutter is forced against the cutting surface to cut the desired shape from the flat workpiece in accordance with the located position of the cutting platen with respect to the cutter.

In accordance with another aspect of the invention, the drive means as defined above include a drive member movable by a binary fluid motor including a series of axially aligned fluid actuated units, each of these units includes a cylinder and an extendable piston having a controlled stroke with respect to the cylinder with the respective strokes having a known binary distance relationship with respect to each other. There are means for interconnecting the fluid units of each fluid motor to cause movement of the driven member a rectilinear distance corresponding to the summation of the strokes of the extended pistons of the units in each of the motors. In this manner, a binary coded number can control the fluid motors to translate the drive members, which in turn are movable in guide ways to locate the platen with respect to the cutter. This provides a convenient manner for adjusting the platen in accordance with binary coded numbers. Consequently, the motors can be controlled by digital information indicative of the cutting positions into which the platen is to be adjusted with respect to the cutter.

By providing movable members extending upwardly into guide members, the platen can rest on a separate support element and the moving arrangement for the platen can prevent vertical force against the moving members as they are shifted into the desired cutting positions. Of course, the fluid motors can be at any desired position, which may be intermediate, so that the coded number will determine the next cutting position of the platen without moving the platen from a preselected starting position.

In accordance with another aspect of the invention, one of the fluid motors is initially located in an intermediate position between cutting operations of the cutter. This fluid motor, in practice, is the one operating on the transversely movable member for shifting the platen transversely with respect to the other two generally parallel moving members. In this manner, the platen can be moved in opposite directions from a starting point in a general direction transverse to the basic movement arrangement for the cutting platen.

By employing the device as defined above, the platen can be rotated without rotary drive means. Only translating drive means are necessary and the relationship of these drive means causes rotation of the platen to the desired cutting position with respect to the cutter.

The primary object of the present invention is the provision of a device for translating and rotating a cutting platen with respect to a reciprocal cutter, which device can rotate the platen without a rotary drive unit, operates rapidly, can be controlled by digital signals and need not support the cutting forces in the actual cutting operation or the weight of the cutting platen.

Another object of the present invention is the provision of a device as defined above, which device can be used in a digital machine control system of the type used in cutting cigar wrappers from natural tobacco leaves.

Still a further object of the present invention is the provision of a device as defined above, which device employs drive members movable in a guide track or guide ways on the platen which movement is the translation movement with respect to each of the tracks or ways.

Still a further object of the present invention is the provision of a device as defined above, which device can use binary actuated translating devices for controlling the rotation and translation of a cutting plate with respect to the reciprocal cutter for moving the platen to the desired cutting position in response to digital signals.

These and other objects and advantages will become apparent from the following description wherein the invention is defined in a preferred embodiment for which it can be used.

BRIEF DESCRIPTION OF DRAWINGS

FIG. 4 is a block diagram showing schematically certain general features of the preferred system;

FIG. 5 is a block diagram outlining control concepts employed in the preferred system of the present invention;

FIG. 7 is a schematic, side elevational view showing the scanning mechanism and the transfer arrangement employed in the illustrated embodiment of the present invention;

FIG. 7A is an enlarged cross-sectional view showing certain features of the structure illustrated in FIG. 7;

FIG. 7B is a schematic representation of the light intensity transducer units used in the illustrated embodiment of FIG. 7;

FIG. 9 is a schematic differential circuit which would create light intensity outputs as grahically illustrated in FIG. 8;

FIG. 10 is a chart showing an operating characteristic of the light intensity scanning arrangement employed in an embodiment of the present invention without the preferred modification as contemplated by the system as shown in FIG. 11;

FIG. 11 is a block diagram of the circuit for modifying the video output of the scanning unit to produce an output modified from that of FIGS. 8 and 9;

FIG. 12 is a graph illustrating the operating characteristics of the circuit shown in FIG. 11;

FIG. 14 is a logic diagram illustrating a system for creating transitions in the scanning operation for use as intermediate data in the preferred embodiment of the present system;

FIG. 14A is simplified logic diagram illustrating a transition data combining digital circuit employed in conjunction with FIG. 14 and used in the preferred system;

FIG. 15 is a block diagram illustrating a data transfer system which could employ the data developed by the structure illustrated in FIG. 14 and digital circuitry for processing and inputting such data;

FIGS. 19 and 20 are tabulations of direct memory entered data employed in the preferred system of the present invention;

FIG. 26 is an outline of the computer program steps employed in the preferred system of the present invention;

FIG. 32 is a side elevational view showing the cutting platen in the cutting position;

FIG. 33 is an enlarged cross-sectional view taken generally along line 33—33 of FIG. 27;

FIG. 34 is a graphic view of the cutting table employed in the preferred mechanism of the present invention;

FIG. 35 is a cross-sectional view of the cutting table as illustrated in FIG. 34;

FIG. 37 is a cross-sectional view of the digital motors in the structure illustrated in FIG. 36;

FIG. 38 is a cross-sectional view taken generally along line 38—38 of FIG. 37;

FIG. 39 is a schematic logic diagram illustrating operating characteristics of the structure shown in FIG. 37;

DESCRIPTION OF INVENTIVE CONCEPTS, PREFERRED EMBODIMENTS AND MODIFICATIONS THEREOF

The present invention relates to a method, system and apparatus for cutting one or more profiles, such as cigar wrappers, from a natural leaf, such as a tobacco leaf. A natural leaf has veins, color variations, a stem in most instances, holes and various defects which are not to be included in the profile cut from the leaf. As a general description, the invention relates to the method, system or apparatus for accomplishing this primary objective by using a constructed profile or image of the leaf which depicts the defects, without using any marking arrangement. The system uses this constructed profile or image for selecting the cut position or positions in a manner generally optimizing the number of wrappers and the quality of wrapper taken from the available surface area of the leaf. The basic and total concept of this method, system and apparatus will be explained in detail. The appended claims set forth the inventive concepts relating to this total description which will be separated into areas for illustrating the various aspects of the method, system and apparatus contemplated.

GENERAL CONCEPTS
(FIGS. 1-6)

Figure 1:
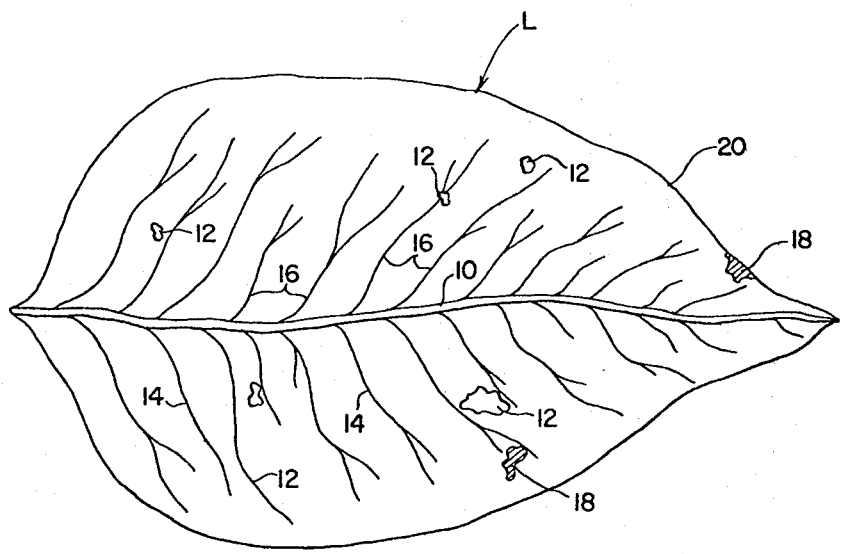
FIG. 1 is a top plan view illustrating a natural tobacco leaf from which the wrappers are to be cut.
Figure 2:
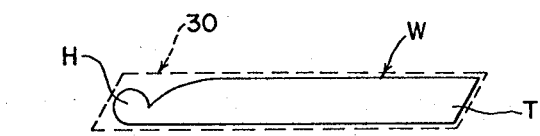
FIG. 2 is a schematic view illustrating the shape of the cigar wrapper to be cut in the preferred embodiment together with the encompassing profile or facsimile shape shown in dashed lines to be used in locating the cut position on the leaf shown in FIG. 1.
Figure 3:
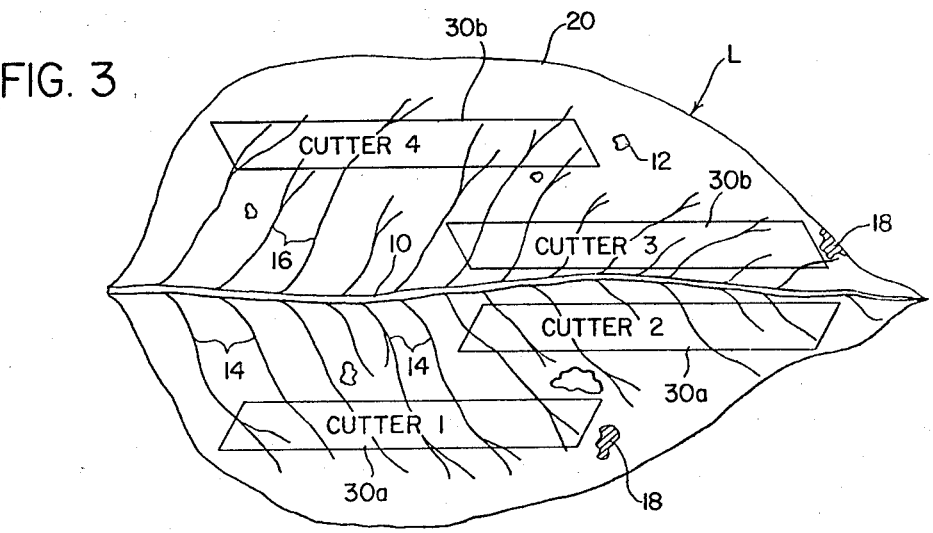
FIG. 3 is a top plan view of the leaf shown in FIG. 1 with the cutter profiles located in cut positions.

Referring now to FIGS. 1-3, a natural tobacco leaf L has known physical characteristics in that it is flaccid, pliable and has internal color variations, energy ray detectable variations and defects like holes, and dark or black areas. In addition, the natural tobacco leaf has a top surface which is to be used as the exposed portion of the wrapper to be cut from the leaf. Natural leaf L is illustrated as including a center stem 10 which extends in a somewhat undulating path longitudinally through the leaf, a plurality of holes 12 of varying size, diagonally extending right and left veins 14, 16, respectively, dark areas 18 and an outline or edge 20. The dark areas 18 may be on either surface of the leaf and are visible from the top surface to a degree determined by their location. Indeed, the dark areas may be internal of the leaf and present only a slight color variation when viewed from the top surface of the leaf. Even in that situation, the dark areas could be considered unacceptable for a wrapper of a cigar. Also, abrupt surface color variations can occur as pronounced light areas in the leaf which may be detectable from one or both surfaces of the leaf and which may be undesirable for a cigar wrapper. From the leaf L cigar wrappers W, as shown in FIG. 2, are to be cut by a cookie cutter type die or clicker die commonly used for cutting of flat sheets in other industries. Wrapper W has a precise shape which allows spiral winding of the wrapper around the binder and/or core of the cigar without producing wrinkles and surface defects. The wrapper generally includes a head H and a portion T called a "tuck". Tuck T is ultimately located in the end of the cigar to be lighted, whereas head H is twisted and wrapped into the portion of the cigar to be held in the smoker's mouth. These shapes are critical and it should be free of dark areas, any holes and heavy veins. The shape of wrapper W, which varies for different length and shaped cigars, can be circumscribed by a four-sided profile 30. The profile is different for left and right hand wrappers and are configurations 30a, 30b, as shown in FIG. 3. Th cutters are labeled CUTTERS 1-4. In this illustrated embodiment the cutters outlined by the shapes 30a, 30 b represent cut positions of the same wrapper shapes. In some instances two or more wrapper shapes could be cut from a single leaf. For the purpose of describing the present system, the cutter to be used in the wrapper has the shape of wrapper W; however, the profile 30 or profiles 30a, 30b are used to locate the cut positions for the wrappers on the surface of leaf L in a manner to avoid any unwanted defects in the resulting wrapper within the confines of general profiles 30a, 30b. In producing wrappers W from leaf L the wrapper profile must be located on the leaf to avoid defects such as holes, the stem, dark areas, color variations of a given magnitude and other such contingencies to produce a wrapper having the quality set forth in the introductory portion of this application. In most arrangements for cutting the wrapper W from a natural tobacco leaf, the stem is removed and the leaf halves are booked or stacked according to the right hand vein arrangement or the left hand vein arrangement. The present system does not contemplate the stemming of the leaf; however, it could be stemmed and a half of a leaf could be processed in the present system. Throughout the rest of the discussion of the present system, wrapper profile 30 is used to locate the cut positions on leaf L of the cutter for a wrapper W since the placement of this profile at various non-conflicting locations will provide proper cut positions for the circumscribed actual wrapper configuration. In practice of the present system, the actual profile 30 or profiles 30a, 30b are slightly greater in size than the contour of the wrapper cutter so that the cut made by the cutter itself will not be at the edge of the leaf or closely adjacent a prohibitive defect to be excluded. In other words, the profile used in selecting the cut positions in accordance with the system herein described is slightly larger than the actual cutter profile used in making the wrapper cut in leaf L so that the cut is offset at least a small amount from the outline of profile 30.

In accordance with the system contemplated by the present invention, a profile or image of the leaf including the outline, stem, surface variations and defects is created and recorded and stored. Thereafter, the profile 30 is manipulated within stored profile or image to locate positions in which the profile 30 avoids unwanted defects and remains in the confines of the leaf. These selected cut positions are then used to control a cutting machine that positions the leaf and wrapper cutter in the desired relative position for a cutting operation to remove the wrapper from the area bound by profile 30 in its final selected position or positions.

A general functional block diagram of the overall system is schematically illustrated in FIG. 4. A description of this block diagram will provide general information regarding the basic concept of the system hereinafter described and can be used as an over view of the system of cutting wrappers W from desired positions on leaf L without requiring the previously used manual manipulation and without sacrificing quality of the resulting wrappers. In accordance with the functional block diagram, a natural leaf is spread onto a vacuum support surface which preferably is capable of transmitting light rays so that the rays pass simultaneously through the surface and through the leaf. These rays are read by a light intensity sensitive device which determines the light intensity at selected locations on the support surface. The total light intensity pattern provides a light intensity profile or image of the natural tobacco leaf supported in a spread condition on the surface. The concept of spreading the natural leaf onto a vacuum support surface for cutting is known and is represented by block 40. The concept of passing light through the leaf supported on a vacuum surface is novel and is represented in block 42. As indicated by block 42, the leaf is indexed or moved incrementally in one direction (hereinafter called the Y direction) and the light intensities at selected areas of the leaf across another direction (hereinafter called the X direction) are recorded at identifiable locations identifiable by both X and Y positions on an imaginary grid on the vacuum surface. The intensity of the light passing through the leaf at these various identifiable locations which cover the total leaf as it has been moved are indicative of the contour of the leaf and color variation or defects including holes, dark areas, the stem, the veins and other surface color variations. By passing light through the leaf, variations on both surfaces are detected as are variations within the leaf which can cause discernible color variations that would be objectionable in a wrapper for a cigar. Block 42 is indicative of this scanning operation for obtaining light intensity at selected locations encompassing the total surface area of natural tobacco leaf L. The scanning operation creates a series of light intensity signals which are each analog voltages. One voltage signal corresponds to each scanned location and appears in line 44. Digital data indicative of the location of the scanned locations simultaneously appears in line 46. The analog light intensity signal in line 44 is converted to digital data indicating whether or not the scanned location has a light intensity value indicative of white, black or an intermediate color, termed "gray". Thus, each of the scanned locations on the leaf, which may be as small as desired and is known as a Pixel, will produce a light intensity, digital signal in line 50. The Pixel data will be white, black or gray. If desired, variations of gray could be obtained; however, such resolution is not required in the present system. The address data in line 46 identifies the location of the Pixel being detected and transmitted in line 50. As can be seen, if the leaf is segregated into a large number of identifiable locations, or Pixels, which have known addresses (in the X and Y directions) and known light intensity conditions, such as white, black or gray, a profile of the leaf itself can be constructed remote from the leaf. For illustrative purposes, a sequencer 60 is indicated as transmitting the digital information regarding the color of the Pixel and the location of the Pixel to any type of storage unit 70 by lines 72, 74. The particular storage arrangement will then contain a matrix indicative of the profile of the leaf including an outline and defects. This data matrix storage unit 70 is indicated to be a sequenced unit incremented by line 469 for each Pixel in the X direction. In practice, storage unit 70 is a direct accessed memory usable by a digital computer in accordance with known computer practice. The indexing by each X Pixel will cover all Y indexes in sequence. Proceeding further into the schematic representation of the general system as shown in FIG. 4, cut locations or positions are determined as represented by block 80 using the stored digital data in storage unit 70. This can be done in a variety of computer arrangements which will be described in more detail later. Basically, a digital representation of the cutter profile 30 is compared to the stored digital profile of leaf L in storage unit 70 and these two profiles are shifted unit the digitized profile 30 does not include a defect, such as a hole, edge of the leaf, or undue color variations. After one cut position is located, a next profile 30 is also shifted with respect to the digitized leaf profile or image in storage unit 70 to locate still a further cut position which avoids the defects set forth above. This process is continued until the digitized representation of profile 30 is set to the extent possible to obtain the desired number of cuts in leaf L. The various cut locations so located by shifting the digitized profiles 30 within the digitized leaf profile of storage unit 70 are in the form X, Y and $\phi$ corresponding to the X, Y location of a selected point on a line of profile 30 and the angle this line makes with the scanned Y direction. The X, Y, and $\phi$ coordinates are then converted to usable cut coordinates represented as X1, X2 and Y by a coordinate arithmetic conversion. This conversion is determined by the usable data necessary to obtain the same X, Y and $\phi$ location on the cutting machine when a linear converting mechanism is used for purposes to be explained later. Arithmetic conversion to cut coordinates usable in the specific machinery contemplated for actually making the cut in the leaf is represented by function block 82. After the scanning operation schematically illustrated as block 42 has been completed, leaf L is transferred to a cutting platen or table. This process is represented by functional block 90. After the leaf has been transferred to the cut platen, the arithmetically generated coordinates from generator 82 are directed through an interface indicated generally as line 92 to a digital-to-analog movement mechanism 100. This mechanism shifts the cut table carrying the leaf to a known cut position determined by coordinates from interface 92. As will be explained later, the movement by mechanism 100 is translated along three axes corresponding to X1, X2 and Y coordinates. The moving to a cut position is represented by block 102. The transfer of leaf L to the cut table is in an oriented position and the cut table is a vacuum surface which holds leaf L in this oriented position. The coordinates from generator 82 operate on the table as they would on the scanning surface. After the leaf and table have been shifted to the first cut position, the wrapper cutter is shifted downwardly to cut a cigar wrapper from the leaf in this first cut position. This action is represented by functional block 104. The cutter is then raised to remove the wrapper from the leaf, which leaf is still held on the table by vacuum. The wrapper is held by a vacuum means as the cutter moves upwardly. This removes the wrapper from the cutting table as represented by functional block 106. Thereafter, the wrapper is removed from the cutter by vacuum transfer arrangement in accordance with known wrapper handling procedures. This functional step is illustrated as block 108. Interface 92 then causes a recycling of the cutter table to the second cut position and a second wrapper is cut, removed and stored for subsequent use. This procedure is continued until all the cuts located within leaf L have been made. Thereafter, the next leaf is processed.

In accordance with the preferred embodiment, while the cutting operation is taking place on one leaf, a second leaf is being spread on the vacuum support surface and scanned and the cut positions are being located and the coordinates X1, X2 and Y are being created. Thus, a tandem arrangement is contemplated wherein the scanning is taking place on one leaf while the cutting operation is taking place on a previous leaf. To facilitate this dual operation, a general control system, as shown schematically in FIG. 5, is employed in the preferred embodiment. The system includes, as basic machine elements, a scanning mechanism 200, a leaf transfer mechanism 202, a locate and cut mechanism 204, a wrapper removing mechanism 206 and a mechanism 208 for removing the spent leaf all the cuts have been made from the leaf. All of these mechanisms, which will be explained in more detail later, are controlled in accordance with a standard practice by a commercially available programmable controller 210, such as one using an Intel 8080 microprocessor. The sequence of mechanical operations are conducted in accordance with the program of the programmable controller in accordance with standard practice in machine control operation. The scanning mechanism 200 provides information to a direct access memory 220 which has a two-way communication with a standard digital computer 240 that locates the cut positions, converts them to X1, X2 and Y coordinates and provides the coordinates to the controller 210. A two-way communication with the programmable controller is provided to load the cut positions into the programmable controller when the programmable controller is ready to accept the cut coordinates for processing a scanned leaf L. The control and function of information provided in FIGS. 4 and 5 is illustrative in nature to show the general process being performed in accordance with the novel system and a general control arrangement which allows the various mechanisms to be operated to cut wrappers from leaf L. This use of a controller 210 reduces computer time and software and provides a standard type of machine control for the various mechanisms used to perform the sequence of events set forth generally in FIG. 4.

Figure 6:
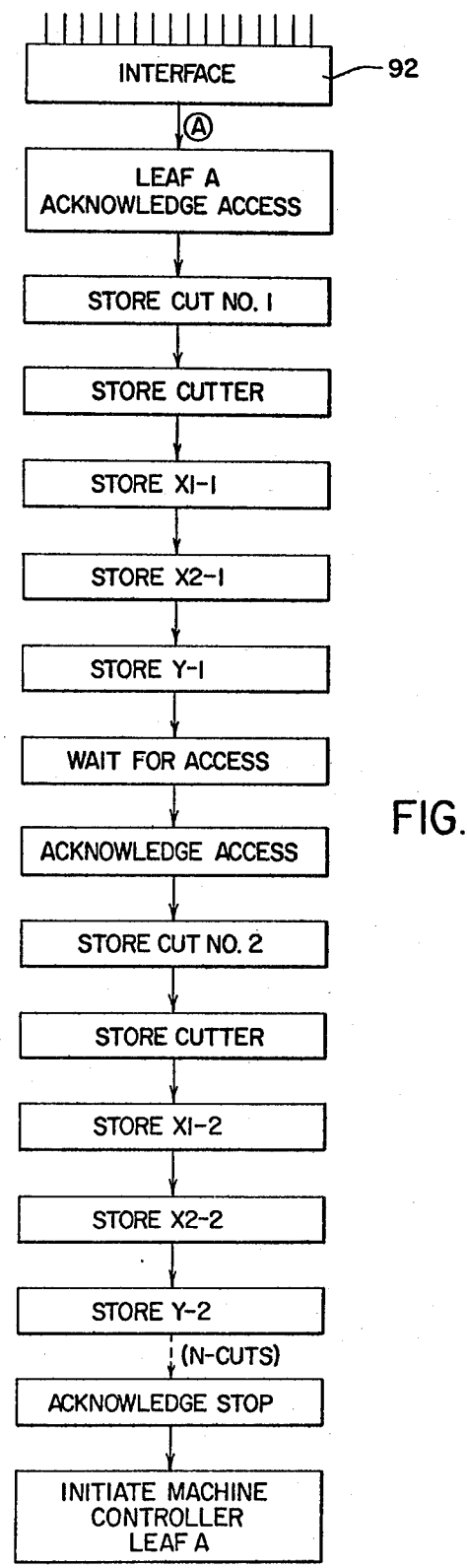
FIG. 6 is a flow chart block diagram illustrating interfacing concepts between the computer and the programmable controller as shown in FIG. 5.
Figure 13:
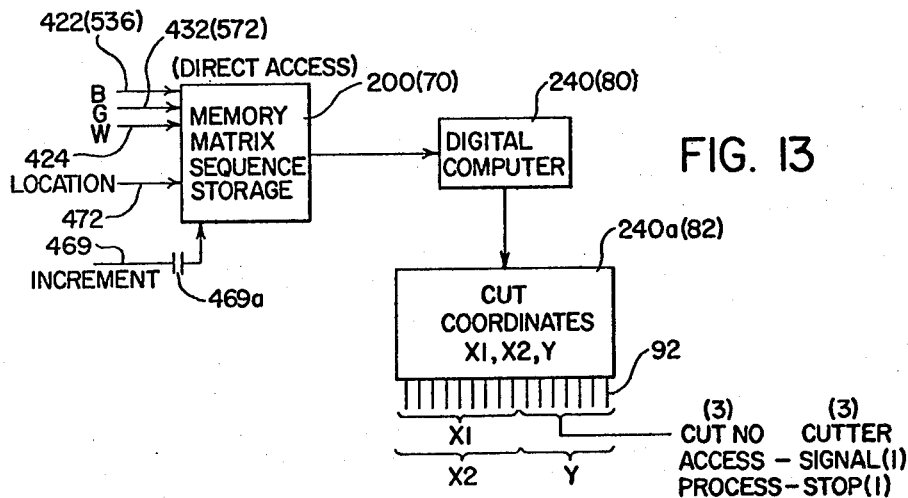
FIG. 13 is a block diagram of the memory loading concept which could be employed in the system when raw data of all locations is used for creating a leaf facsimile.

Referring not to FIG. 6, this figure illustrates, somewhat generally, the interface 92 between the programmable controller 210 and the digital computer 240 as represented in FIG. 5. Also, the information from computer 240 is illustrated in FIG. 13. As a first step, the programmable controller 210 acknowledge that it desires access to the digital computer 240 for data regarding the cut coordinates for leaf designated as "leaf A". Thereafter, the programmable controller obtains and stores the number of the cut (1, 2 ... n), the particular cutter (cutter 1, 2, 3, etc), the coordinates X1, X2 and Y for the first cut. It is possible to use different cutters to obtain different wrapper sizes. For that reason, the particular cutter to be used is inputted to the programmable controller. In addition, as noted in FIG. 3, there are left and right hand wrapper cutters to accommodate the different vein configurations. Thus, if a cut is to be made from one side of the leaf, one cutter is selected, whereas another cutter is selected for a wrapper from the other side of the leaf. Because of this, the programmable controller receives information regarding which cutter is to be used, which cuts are to be made and where the cut is to be made on the leaf. Thereafter, the programmable controller waits for access again from the computer, acknowledges access and receives the information regarding the second cut. This continues until the programmable controller receives information regarding all n cuts to be made in leaf A. At that time, the programmable controller acknowledges that all information has been received with respect to leaf A and proceeds to initiate the controller for processing leaf A. After leaf A has been processed, the programmable controller then receives information regarding the cut positions and cutters from the digital computer for making the cuts in the next leaf. The cutting operation is proceeding as the scanning operation for the next leaf is proceeding. FIGS. 4, 5 and 6 are to be taken together to illustrate one arrangement for accomplishing the system contemplated by the present invention. The details of the system will be hereinafter set forth. However, it should be appreciated that there are several machine control arrangements and computer arrangements which can be employed in practicing the method and system contemplated by the description herein.

SCANNING AND CREATING DIGITAL FACSIMILE DATA

(FIGS. 7, 7A, 7B and 8–12)

As explained with respect to the general description above, a system in accordance with the present invention involves an arrangement for obtaining digital information regarding the light transmitted characteristics at various identifiable locations or Pixels (X, Y locations) on a natural tobacco leaf L for processing of this information to select available cut positions for one or more cuts to be made in the tobacco leaf in the process of forming wrappers for cigars. As indicated in the block diagram of FIG. 4, used for illustrating certain basic concepts of the system under consideration, block 42 contemplates a scanning mechanism schematically represented as mechanism 200 in the control concept block diagram shown in FIG. 5. A variety of mechanisms 200 could be employed for the scanning operation to produce the desired digital information. One of the basic concepts of the present system is the generation of a signal, preferably digital, indicative of the surface or color condition of selected, known locations or Pixels on the tobacco leaf, which Pixels can be combined and processed in a manner generally described above to give a representative facsimile, image or profile of the leaf including both color variations and defects such as holes and dark areas and stems. This facsimile, profile or image is then used to graphically or arithmetically locate the particular cut positions for subsequent cutting of wrappers from the natural leaf. To produce digital information or data regarding the surface condition or color variation at locations on leaf L, mechanism 200 is used. This mechanism is schematically illustrated in FIGS. 7, 7A, 7B, 8 and 9 which show the preferred scanning operation. In accordance with this illustrated embodiment, there is provided a continuously driven belt 300 movable around spaced support rolls 302, 304 and having an upper surface 300a and a lower or inner surface 300b. For the scanning operation, the belt is transparent or translucent so that it can transmit light rays through the belt for a purpose to be described later. In practice, this belt is translucent and formed from a material known as "Revo" which is a clear nylon belting supplied by L. H. Shingle Company and has a general thickness of 0.04 inches. This standard nylon belting is provided with small perforations 300c extending through the belting to develop a positive pressure differential adjacent upper surface 300a when a vacuum is created adjacent lower surface 300b. The use of the vacuum at surface 300a holds leaf L in a manually or machine spread condition on leaf receiving surface or support surface 300a in the "scan" position shown in FIG. 7. To drive the belt in a clockwise direction, as shown in FIG. 7, there is provided an appropriate electric motor 306 connected to roll 302 by a drive mechanism schematically represented as dashed line 308. An encoder 310 provides pulses in output line 312 when motor 306 has driven belt 300 axially a preselected distance. In practice, this preselected distance is 0.05 inches. Consequently, an encoder pulse is provided after each movement of 0.05 inches of belt 300 in the Y direction indicated in FIGS. 7 and 7A. Below the belt in both the "scan" and "transfer" positions there is provided a vacuum box 320 of somewhat standard design in the cigar making industry. This vacuum box substantially traverses the "scan" and "transfer" positions of the upper run of belt 300 between rolls 302 and 304. If the leaf is to be placed on belt 300 in the lower run, a vacuum box could be provided along this run and roll 302 could be a standard vacuum roll. Adjacent the scan position there is provided a vacuum chamber 322 which is maintained at a vacuum by an appropriate external vacuum source. In the transfer position, there is provided a chamber 324 which combines with chamber 322 to form the total box 320. A pressure sensitive flapper valve 326 separates chambers 322, 324 to allow selective transfer of the leaf by a mechanism 202, which will be explained later. The leaf is to be removed from upper surface 300a of belt 300 in the transfer area after it has been scanned. Transfer chamber 324 can be provided with a vacuum or with pressurized air. After a leaf has been scanned, it is moved to the transfer position. At that position chamber 324 is pressurized. This allows the scanned leaf to be grasped by a vacuumized transfer head 328. This head has a lower vacuumized leaf receiving surface that holds the leaf L in an oriented position and transfers it to the cutting table in a manner to be described later. Thus, to transfer the leaf from belt 300 to transfer head 328 pressure is applied to chamber 324 and vacuum is created adjacent the lower surface of transfer head 328. This transfer head and procedure is used often in the tobacco industry to transfer tobacco products from a belt to another structure. When pressure is applied to chamber 324, valve 326 closes to prevent loss of vacuum in scanning chamber 322. Of course, other arrangements could be used for holding leaf L by vacuum onto a scanning surface while the surface is being moved and then for removing the leaf from the scanning surface; however, the arrangement illustrated in FIG. 7 is now contemplated for use in the present system. Belt 300 is stopped momentarily for leaf transfer.

In accordance with the preferred embodiment of the present invention, scanning device 200 includes any appropriate mechanism for identifying the color content or the light intensity characteristics at various preselected locations or Pixels across the face of tobacco leaf L at X and Y positions. In practice, the data creating mechanism is a scanning head 340 which simultaneously records light intensity at spaced locations across belt 300 in a direction, identified as the X direction in FIG. 7B. The X direction is generally orthogonal to the longitudinal or Y direction shown in FIGS. 7 and 7A. In essence, the scanning head 340 receives light rays along a selected Y position which is indicative of the light intensity veiwed at given spaced positions across the leaf. The term "scanning" as used in conjunction with mechanism 200 and head 340 means that these positions are read in series although they may be simultaneously detected. The scanning feature is provided by the circuit shown in FIG. 8. The light intensity at most locations in both the X and Y directions of leaf L is measured and an output is created representative of this light intensity. Of course, certain approximations are acceptable. Locations in the X direction are viewed by head 340 at spaced lines or positions in the Y direction. This can create certain small bands of undetected areas between adjacent Y positions. This feature is minimized by shifting or moving the scanned position only a small distance in the Y direction. This will provide sufficient digital information or data for identifiable locations on the surface of leaf L to create leaf profile for location of the profiles 30. In practice, a LC 100 512 EC Reticon detecting or scanning head 340 is employed. This type of unit is commercially available from Reticon Corporation of Sunnyvale, California. In this type of mechanism, a lens 342 directs light rays from the surface of leaf L into an elongated aperture 344. By using the lens, the view distance in the X direction at the leaf area is focused onto 512 transversely spaced light intensity sensing units 350 each having a width approximately 2 mils. Consequently, the light profile in the X direction at a given Y position is focused on and changes the charged characteristics of the light intensity sensitive units 350 schematically illustrated in FIG. 7B. In this manner, light intensity at 512 different indexed or shifted positions in the Y direction of belt 300 are read simultaneously by the separate units 350. This covers the total leaf width and much of surface 300a. The Reticon unit uses a clocking pulse to step a shift register which allows serial reading of the light intensity data of each 512 units 350. This serial output is an analog video output as described in FIG. 8. The voltage of this video output is an analog representative of the light intensity exposed to each of the units 350 spaced in the X direction at a given Y position. The setting of units 350 in a given Y position is not scanning; however, the output from the Reticon unit is a scanning function since it reads successive cells or units 350 and outputs them in series as representative of the light intensity condition viewed by the units across a given Y position. After all units 350 have been read, scanning unit 350 is ready to receive the light intensity at selected positions across the next adjacent Y position of leaf L. To do this, belt 300 moves leaf L by motor 306. As will be explained later, encoder 310 produces a signal in line 312 which indicates that the units or cells 350 are now ready to read the light pattern across the next successive longitudinally spaced position on surface 300a which carries and supports leaf L. By progressing the belt 300 in the Y direction, the output of the Reticon sensing head 350 reads the identifiable transverse locations on surface 300a at the various orthogonally spaced positions in the Y direction. The spacing between the units 350 and leaf L is such that a distance of approximately 12.5 inches is focused by lens 342 onto the 512 light sensitive units. This provides a spacing in the X direction of approximately 0.025 inches as compared to a spacing of approximately 0.05 inches in the Y direction as determined by the adjustable setting of encoder 312. As is known, the 512 units or cells 350 are approximately 2 mils in width; therefore, the spacing of the units from the leaf and the lens produces a scan or viewing field in the X direction of slightly over 1:10. Other arrangements could be used to change the viewed field across leaf L. The setting of unit 340 to provide a unit or cell 350 for each approximately 0.025 inches has proven satisfactory and provides an identifiable location, or a Pixel, which is satisfactory in size. The Pixel has Y direction dimensions of approximately 0.05 inches to give good resolution for the ultimately constructed image or profile of the leaf L. The output of the Reticon unit for each of the Pixels in the X direction is a video signal having a voltage level indicative of the sensed light intensity at the individual cells 350 being read by the Reticon unit in accordance with standard practice for this type of unit. As so far described, scanning head 340 has produced an analog signal for each of 512 positions across the surface 300a of belt 300 for a given location of the belt in a Y direction. As the belt is moved by motor 306 to a next position creating an encoder output in line 312 this process of providing output analog signals for 512 positions in the X direction is repeated. This action is continued until the total leaf has been processed. In practice, there are 512 Y direction positions to combine with the 512 X direction positions. Since the Y direction positions are substantially twice as great as the X direction positions, the identifiable locations are more highly resolved in the X direction. The surface area on belt 300 being viewed by scanning head 340 measures approximately 12 inches across and about 25 inches in length. This is sufficient to encompass natural tobacco leaves of the type used in producing wrappers for cigars. This monitored field of view of course can be changed by the optics of the scanning operation and by changing the number of Y direction positions used to complete a total scan of the surface 300a carrying a leaf L. The belt can move continuously at a rate allowing Pixel reading.

To provide discernible light intensity for viewing by head 340, it is possible to light the leaf on belt 300 by appropriately spaced lights 352 schematically illustrated as arrows in FIG. 7A. These lights can be at angles to accentuate such surface conditions as veins or can be perpendicularly directed toward the leaf surface. In any instance, this front lighting arrangement does not allow head 340 to detect certain surface defects, such as discoloration and defects within the leaf itself and certain color variation on leaf surface. To provide a more accurate light intensity profile of the total leaf, the preferred embodiment of the system uses a back lighting arrangement wherein light rays are passed simultaneously through belt 300 and leaf L. This procedure produces high resolution light intensity profile at the detecting cells 350. This back lighted profile is more nearly indicative of the actual condition of the surface of the leaf, together with certain conditions which may be within the leaf or on the opposite surface of the leaf. Thus, one aspect of the system, as contemplated for use in practice, is back lighting of the leaf to pass visible light rays or other detectable energy rays through both the belt 300 and leaf L. In accordance with this aspect of the novel system, there is provided a transversely extending apertured fluorescent light 360, with the elongated apertured window of the light extending generally parallel to the aperture 344 controlling light flow to the units or cells 350. This aperture in unit 340 is approximately 17 mils in width. The light rays from the apertured fluorescent light 360 are directed through belt 300 and leaf L, if the leaf is over the light, and into aperture 344. An apertured fluorescent light for use in the system is a stock item available from various sources and has an opening of approximately 30° and a reflective surface around the remainder of the interior surface of the light. This gives a directed light source aligned with the aperture 344. Light 360 is fixed with respect to scanning head 340 by an appropriate mounting arrangement including a shield 362. This shield further restricts the deflection of light from the area of the belt to be illuminated. In FIG. 7A, an appropriate device, such as a photocell 370, is used to detect the leading edge of leaf L as it is conveyed by belt 300. This photocell creates a "start scan" signal in line 372 which will be used in the circuit illustrated in FIG. 8 for the purpose of starting the scanning operation.

Figure 8:
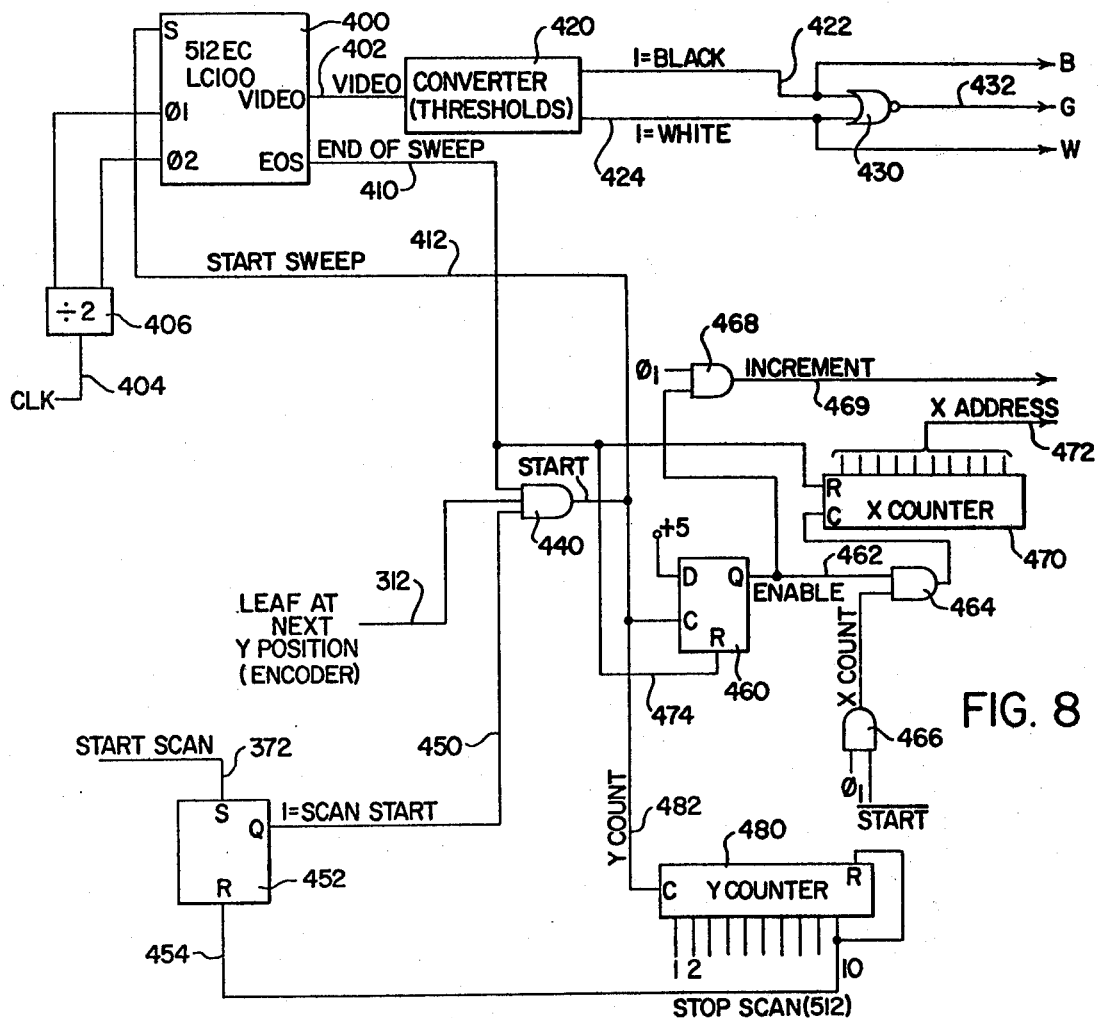
FIG. 8 is a logic diagram illustrating in block diagram and logic diagram form the control system for the scanning operation to be employed in the structure as schematically illustrated in FIGS. 7, 7A and 7B.

Referring now to FIG. 8, a general scanning and output logic diagram for obtaining digital output facsimile data from the operation of scanner head 340 is illustrated. In this illustrated logic circuit, the standard Reticon reading device 400 is used to provide a series of analog data bits on line 402 which correspond to the X Pixels which are outputted in series by an external clocking pulse on line 404. These clocking pulses are divided by an appropriate divider 406 to produce two input clocks $\phi1$, $\phi2$ for controlling the scanning operation of the sequential reading device 400. This sequencing device employs a shift register to read each of the different units or cells 350 and to output an analog voltage on line 402 for each cell. At the end of a sweep across the cells, there is logic 1 produced in the end of sweep (EOS) line 410. The clock at line 404 may have a variety of frequencies; however, in practice it is in the range of 100 Kilohertz to 1 Megahertz according to the speed of the output signal required. Since a subsequent sweep is controlled by movement of the belt 300, as shown in FIG. 7, a rapid sweep through the 512 Pixels is employed. A conversion circuit 420, best shown in FIG. 9, produces a digital logic 1 in line 422 when the light intensity of a Pixel being read produces an analog voltage in line 402 less than a preselected voltage level. This logic 1 is indicative of a "black" condition for a Pixel. In a like manner, if the analog voltage of a Pixel is above a certain voltage level, which is indicative of a white condition, such as no leaf or holes in the leaf, a logic 1 appears in line 424. This is termed a "white" Pixel condition. A white or black condition indicated by the logic in lines 422, 424 control NOR gate 430 which produces a "gray" digital signal in line 432 when there is neither a black or white signal. Thus, a Pixel being read produces either a black, white, or gray digital output signal indicative of the light intensity at the Pixel. The gray signal is generally indicative of the natural color of the leaf being exposed to a cell 350. At the end of each sweep, a logic 1 in line 410 stops the video output at line 402. The sequencer 400 is initiated for a subsequent sweep by a logic 1 at the start terminal S. To create a logic 1 in the start line 412, there is provided an AND gate 440 having three inputs. Th first input 312 is the output of encoder 310 shown in FIG. 7. A signal appears in line 312 when the leaf is in the next Y position for a subsequent scan in the X direction. The second input to gate 440 is line 410 which is enabled when a prior sweep has been completed. The third input is line 450 which is a logic 1 during the scanning operation. A logic 0 in line 450 prevents scanning. A variety of circuits could be used for controlling the logic of line 450; however, in the illustrated embodiment, a flip-flop 452 is set by a logic 1 in line 372 from the photocell 370 shown in FIG. 7A. Thus, when a leaf is moved by belt 300 into the scanning position, a logic 1 appears in line 372. This sets flip-flop 452 to enable gate 440. After the desired number of positions in the Y direction have been processed, in practice 512, a logic 1 appears in line 454. This resets flip-flop 452 and shifts a logic 0 into the line 450. This disables gate 440. Sweep start signals in line 412 can not be created until the next leaf sets flip-flop 452. Consequently, at each Y position a logic 1 is created at the output of gate 440 by line 312, if a leaf is being scanned. This starts the next X sweep. A logic 1 in line 412 not only starts a sweep, but also clocks flip-flop 460 to produce an enable signal in line 462. This enables X counting gate 464, controlled by gate 466, and enables increment gate 468. This latter gate is optional for a purpose to be described later. A logic 1 in line 412 up counts Y counter 480 by pulsing Y count line 482. All of these functions are caused by a signal in line 312 as long as gate 440 is enabled by lines 410 and 450. As soon as a sweep has started, a logic 0 appears in the line 410 which inhibits gate 440 until the X sweep has been processed.

During an X sweep, output pulses are created in lines 422, 424 or 432. With each pulse, gate 466 clocks gate 464 to up count X counter 470. This produces the X address of the Pixel being read at the output of X counter 470. At the end of the X sweep, not only is gate 440 enabled, but X counter 470 is reset for the next sweep and flip-flop 460 is reset by line 474. This reset produces a logic 0 in the enable line 462 to disable counting gate 464 and incrementing gate 468. When Y counter 480 reaches a count of 512 the Y counter is reset. Line 454 resets flip-flop 452 to indicate that the scan is completed. Flip-flop 452 then prevents further scanning until the next leaf is available for processing.

In operation, for each sweep, the light intensity value of the Pixel and the X address of the Pixel is available at the output of the circuit shown in FIG. 8. This information is available for each sweep until the Y counter has indicated that the desired number of X sweeps has been completed. At that time, the sweep circuit is deactivated until the next leaf is available for processing. The Y counter could be used to input the Y addresses for any given Pixel. In other words, the X address in lines 472 from X counter 470 could be combined with the output of Y counter 480 to give not only the X address for the Pixel, but also the Y address. The Y address is not generally required in the illustrated embodiment of the invention because it is sequenced in series.

Referring now to FIG. 9, the converter 420 is schematically illustrated as including two differential amplifiers 490, 492 poled as shown and having voltage adjustable rheostats 494, 496 to control the respective negative terminals. An inverter 498 inverts the output of amplifier 490 to produce a logic 1 in line 422 when a condition designated as "black" by rheostat 494 has been reached. Other arrangements could be used to convert the analog video signal in line 402 to a digital logic indicative of the black or white conditions. Referring now to FIG. 10, this is a graph of a single X sweep across the leaf at a selected Y position. For illustrative purposes, the leaf has a center stem 10 and a hole 12. It is noted that opposite edges of the leaf are indicated by a white signal in line 424. The black stem is indicated by black signal in line 422. The hole 12 is represented by a white signal in line 424. Inbetween these extreme positions, logic 1 appears in line 432. This provides the general profile for the remainder of the leaf which does not exhibit either a drastically white or a drastically black condition. A sweep as illustrated in FIG. 10 will be repeated 512 times for each leaf L and the information provided during each sweep can be used to create a profile of the leaf indicating the defect areas which should be avoided when locating a wrapper cut position on the leaf.

In practice, it was found that the procedure for obtaining black and gray Pixel information by comparing the light intensity with a fixed value for determining black presented some difficulties, especially when the color of the leaf changed or the conditions of the light or cells 350 varied. Consequently, in accordance with another aspect of this system a modified black signal is obtained by comparing the Pixel light intensity with a controlled average voltage. This average voltage uses the analog signals at line 402 for a majority of the Pixels. By comparing an analog Pixel voltage with an average voltage for prior Pixels, a black signal is recorded when there is in fact a substantial black condition compared with the operating conditions of the scanner and the color of the leaf. A circuit developed for obtaining this modified black signal is schematically illustrated in FIG. 11. In this figure, the black modification conversion circuit 500 includes an automatic gain control, or amplifier, 502 which amplifies the analog Pixel voltage from line 402 and directs it to line 504. The automatic gain control or amplifier 502 is not needed in certain instances; therefore, it is enabled only when required by a gate 506. This gate has inputs 510, 512 connected by inverters 514, 516 with the output lines 422, 424, respectively, of conversion circuit 420 previously described. If the previously described conversion circuit produces a white signal, a logic 0 is directed to gate 506 and amplifier 502 is not activated. If a black signal is created in line 422 the automatic gain control or amplifier 502 is deactivated and held deactivated for a time delay indicated by the block 520. This time delay retains the black signal for a set time, which is 0.1 seconds in practice. In other words, gate 506 is deactivated whenever a white signal is created by circuit 420 and is held deactivated whenever a black signal is received. This allows the automatic gain control to be inactive when the sweep is mostly white, such as when there is no leaf or only a minor portion of the leaf is being detected by the sweep in the X direction. In this manner, the averaging concept does not become over weighted in a white voltage direction.

A differential amplifier 530 has inputs 532, 534 and an output 536 which receives the modified black signal. The voltage at input 534 is determined by the accumulated average of the Pixel voltage in line 504 as averaged by circuit 540. This is a capacitor averaging circuit in practice. The voltage of the capacitor averaging circuit is offset downwardly by an appropriate offset circuit 542. Consequently, the voltage at the input 534 is the average of the Pixel voltages, but offset downwardly for a reason to be explained later. To prevent the Pixel average voltage captured in circuit 540 from being distorted by white signals and black signals, there is provided a white exclusion circuit 550 which is adjustable as indicated by circuit 552. In a like manner, a black exclusion circuit 560 is provided with an adjustment circuit 562. Circuit 540 receives no signals when gate 506 is disabled because of mostly white being recorded. The circuit 550 removes those white areas which are not too large, such as a small hole.

The modified black output line 536 and line 424 are directed to NOR gate 570 to produce a gray Pixel data in line 572 when there is no white or modified black signal. During normal X sweeps across the leaf, the amplifier 502 is operative. It is only inoperative when there is a prolonged period of white. This removes from the averaging function the predominantly white area of surface 300a surrounding the leaf being scanned or the white area of a large hole. As shown in FIG. 12, averaging circuit 540 captures an average voltage indicated basically by the line 580. This average voltage line excludes the black portions and white portions indicated by the legend OFF either by disabling amplifier 502 or by exclusion circuits 550, 560. Offset circuit 542 offsets the average voltage downwardly to a level shown as line 582 which is the voltage used as a comparison voltage for the Pixel voltage in line 532 to determine a modified black output. By offsetting the average voltage downwardly, only light intensities which are lower than the offset average reference voltage in line 534 (line 582 of FIG. 12) will produce a black signal. A white signal is produced in accordance with the conversion circuit 420 as previously described. By using the circuit as shown in FIG. 11 and graphically depicted in FIG. 12, a more accurate color profile in the X direction is obtained. As can be seen, the average voltage from a prior X sweep remains in the circuit 540 for the starting point of the next sweep. In this manner, if a group of dark leaves are being scanned, black defects can be detected. In such an instance, a fixed data voltage for detecting the black areas could indicate the total leaf is black. Of course, it would be possible to adjust the fixed black data for darker leaves or changes in the response of scanner 340 to overcome some of this difficulty; however, the circuit 500 of FIG. 11 automatically makes appropriate compensations. FIGS. 9 and 11 could be modified to give more than one shade of gray if needed.

As so far explained, the scanning system creates three output signals which are black, gray and white that are digital signals with a given logic indicating the existance of one of these colors for a particular Pixel which has an X address for a given Y position. As the scan is continued, the color profile of the total tobacco leaf being processed is obtained by a series of signals indicating the shielding effect or the light intensity of various identifiable locations or Pixels across the total surface of the leaf and also across those portions of surface 300a which are in the scanning pattern, but are not covered by a leaf.

GENERAL DATA PROCESSING
(FIGS. 4, 5, 6 AND 13)

As so far described, raw data is obtained for each Pixel or identifiable location during the scanning operation and this raw data is available at the output lines of the structure shown in FIG. 8 or as modified by the showing in FIG. 11. This data includes the color intensity of a given location or Pixel and the address in the X direction across the surface 300a. This information can be stored in sequence in standard READ/WRITE memory through a normal direct acessing to the memory units used in digital computers. In other words, the raw data can be stacked in sequence in the storage unit 70, shown in FIG. 4 which corresponds to the direct access memory 220 of the control concept as illustrated in FIG. 5. This feature of storing data relating to the color intensity of each Pixel is schematically illustrated in FIG. 13 wherein the increment line 469 is used to index a direct accessed memory after each Pixel voltage signal is processed by the converter 420 and provided as a white, black or gray signal. To allow time for settling of the Pixel information in lines 422 (536), 432 (572) and 424 a time dealy arrangement can be provided. This is schematically illustrated as a time delaying capacitor 469a. As so far described, Pixel data bits for all X Pixels are stored in the direct access memory for each Y line or position. Since each of the Y lines is stored, the Y address from counter 480 shown in FIG. 8 is not required. Indeed, with the raw data being provided to the direct accessed memory, the X address would not be needed since a particular location in memory would be assigned to each of the Pixels both in the X and Y directions. As will be explained in accordance with the illustrated embodiment of the disclosed system, the X address is required because not all the Pixels are stored. In addition, the X address would be valuable information for processing the leaf profile in most software arrangements. Digital computer 240 uses the stored profile data in the memory unit to locate and arithmetically convert cut coordinates as represented by block 240a in FIG. 13. This function block corresponds to the processing block 82 of FIG. 4. The cut coordinates employed in the preferred embodiment are X1, X2 and Y which are used in the cutter adjusting mechanism of the preferred embodiment as will be explained later. In other words, each cut position is located by three linear coordinates which are identified for the purposes of description as X1, X2 and Y. These coordinates are provided as eight bit digital words each of which will control a linear moving mechanism in accordance with the magnitude of the digital number contained in the word. The digital computer also indicates the number of the cut and the particular cutter used together with an ACCESS signal and a PROCESS stop signal, as schematically illustrated in the general process chart of FIG. 6. Essentially, the present system stores data relating to the profile of the leaf and its defects in a manner which can be processed to locate the cut positions within the created profile image of the leaf. The leaf itself is not used in the location of the cutter positions. The processing of stored data to locate the cut positions is well within the general technology of the computer art when the memory has been loaded in accordance with the present system. Hereinafter, certain programming techniques will be discussed which simplify the cut location procedure used by the digital computer; however, various other arrangements could be employed for the cut location to develop cut coordinates for each cut.

TRANSITION CONVERSION
(FIGS. 14 AND 14A)

As so far described, raw data indicative of the color of each Pixel has been created. This information could be used for controlling the cutting equipment as hereinafter described by locating the wrapper cut positions based upon this raw data. However, in accordance with the preferred embodiment of the invention, the raw data is not required. As long as there is raw data indicating white in the Pixels, the leaf has not been reached or a hole or white defect is being viewed. The same is true regarding a succession of gray or black raw data signals. Thus, to reduce the stored data necessary for constructing the profile or image of leaf L, the present system employs data indicative of color transitions. This transition data information can be obtained in a variety of ways between the output of surface shown in FIG. 8 and the input to the storage memory. This involves a digital circuit interfacing the scanner with the memory unit. A digital circuit for creating transition data and usable between the scanning circuit of FIG. 11 (FIG. 8) and the memory units is illustrated in FIGS. 14 and 14A. Referring now to FIG. 14, transition flip-flops 600–605 are reset when a pulse of the identified color is created. These flip-flops are set when a given color pulse is created. Consequently, the resetting of one of the flip-flops to create a logic 0 output indicates a color transition at the Pixel being processed. Upon the receipt of a reset pulse, the transition storing flip-flops 610–615 are clocked to produce a transition signal in lines 620–625 as indicated. On each φ2 pulse, the storage flip-flops 610–615 are strobed back to the reset condition. The input lines of the circuit shown in FIG. 14 are the output lines of the preferred embodiment circuit shown in FIG. 11. The output lines 620–625 receive a pulse when a transition is made from one color to another color at a given Pixel during an X sweep across surface 300a. If the transition given both the "to" and "from" colors is to be used in constructing the leaf profile for processing, the signals in lines 620–625 could be used directly; however, in practice, it is only necessary to know that there is a transition to a given color such as black, gray or white. Consequently, lines 620–625 are assimilated to determine whether or not there is a transition to black, to gray or to white. Various intermediate digital circuits could be used for this purpose; however, in FIG. 14A OR gates 630–632 having outputs 633–635, respectively, are employed. Gate 630 has an output when there is a transition to black. In a like manner, gate 631 has an output when there is a transition to gray, and gate 632 has an output when there is a transition to white. By using a digital system for determining transitions before the information is stored into the direct accessed memory, a substantially reduced number of storage locations are required to provide the necessary information for the total profile of leaf L. When transitions are being used the X address appearing on line 472 of FIG. 8 is required. This determines the X position at which a transition is made to a given color. If the stem is being detected, there will be a transition to black at a given X position and then a transition to gray after the stem has been passed. The same arrangement is used for defects, surface variations and the edge of the leaf to determine the profile of the leaf without using the raw data of all Pixels. The computer would have access to the transition information; therefore, the color of any Pixel between transitions would be known from the stored transition information. Consequently, transition data is used to save memory capacity. The transition circuitry shown in FIGS. 14 and 14A is in a digital circuit between scanning circuit 200 and direct access memory 202 as schematically shown in FIG. 5.

FACSIMILE DATA INTERFACE AND DIRECT ACCESS STORAGE THEREOF

(FIGS. 15–20)

As indicated above, the raw data developed by the scanning operation can be converted into transitions by an intermediate digital circuitry between the output of the circuits of FIGS. 8 or 11 and the actual memory used for storing the data. Also included in this intermediate digital circuitry for processing transitions instead of raw data developed by the scanning process are digital transition transferring devices of the type schematically illustrated in FIGS. 15, 16 and 17. These transfer devices direct the transition information or data to specific memory locations, as schematically illustrated in FIG. 18. FIGS. 19 and 20 are schematic representations of the data actually stored in the memory. If the transition data is indicative of the actual transition from one color to another color, the data can be processed in accordance with the digital circuitry illustrated in FIG. 15. In this circuitry, a sixteen bit accumulator 630 counts each transition pulse through a line 632. At the end of a scan, the reset line 454 resets accumulator 630. The output of the accumulator is illustrated as lines 634, which include sixteen lines to read the stages of accumulator 630. This digital data is directed to the input of a data transfer chip 640 having a sixteen bit output 642 and a data transfer terminal T activated by lines 644 which is the EOS line 410. To provide a certain time delay between the EOS pulse and the indexing of the direct accessed memory, there is provided a device, such as one shot device 646 having an output 648. the output indexes the memory to a next location into which the next accumulator data from lines 642 is stored. In operation, for each X sweep, the transitions are accumulated in accumulator 630. At the end of the sweep, the accumulated number of transitions is inserted into the memory and the memory is indexed. This continues for 512 sweeps in the X direction so that the memory has 512 sixteen bit words that are the accumulated number of transitions for each of the several Y positions of the scanning operation.

To transfer the transition data, the transitions and the X address thereof are directed to the inputs of a data transfer chip 650 having sixteen outputs 652 and a transfer terminal T controlled by line 654. OR gate 656 receives a pulse at each transition which pulse is delayed slightly by a device, such as capacitor 657, to then transfer the input data to the output lines 652 of transfer chip or device 650. An appropriate time delay 658 then allows indexing of the X memory unit by a signal in line 659. Thus, at each transition in the X direction, the address of the transition appearing in line 472 is transferred through the sixteen bit output 652 together with the type of transition. Thus, the X memory unit receives a transition and the Pixel address of the transition.

Figure 16:
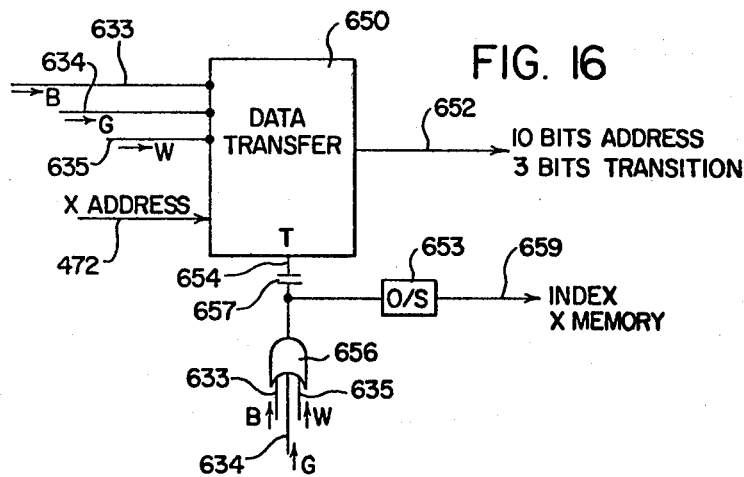
FIG. 16 and 17 are data transfer circuits similar to that shown in FIG. 15 but employing the data developed by the schematic digital circuit of FIG. 14A.
Figure 17:
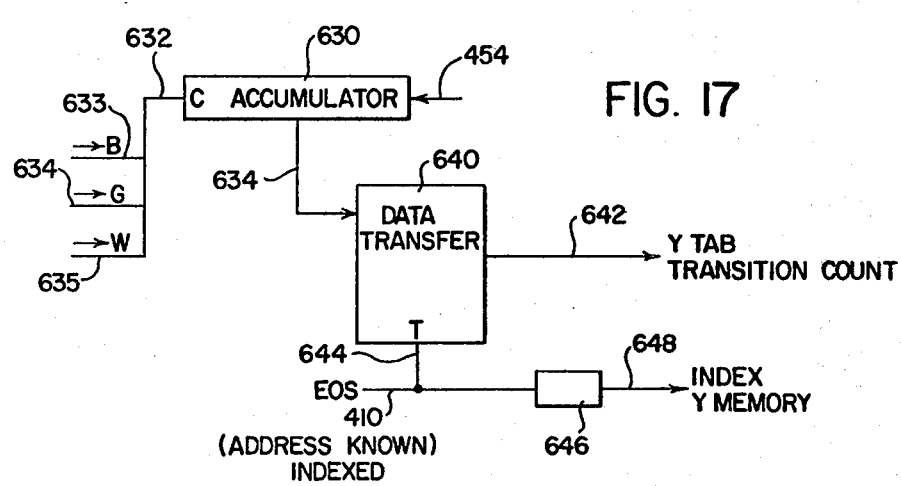
Figure 18:
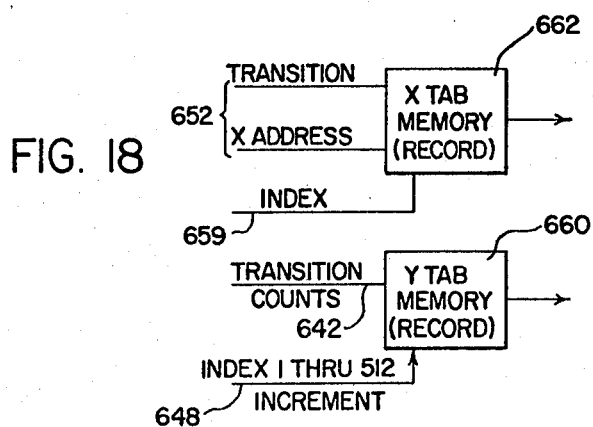
FIG. 18 is a block diagram illustrating the direct access memory loading concept used in the preferred system wherein transition data is loaded into separate memory units or areas.

The circuitry illustrated in FIGS. 16 and 17 is the same circuitry and has basically the same numbers as the circuitry illustrated in FIG. 15. The difference is that the transition information is recieved from the network illustrated in FIG. 14A. There is only three bits of transition information or data, which data determine and record the type of transition. Accumulator 630 of FIG. 17 still accumulates the same number of transitions; however, the data being transferred through the sixteen bit lines 652 is indicative of the transition to a particular color and not necessarily from which color the transition is being made. The circuitry shown in FIGS. 14, 14A, 16 and 17 is the preferred embodiment. This circuitry is interposed between the raw data scanning circuits of FIGS. 8 and 11 and the direct assessing memory units. This is schematically illustrated in FIG. 18 wherein the direct access memory unit for the Y information is called the "Y TAB" memory 660. The accumulated number of transitions at each of the Y positions is recorded and stored in sequence in this unit. In a like manner, the X information including the type of transition and the Pixel address for the transition is directed to the "X TAB" memory 662. This memory is indexed at each transition. Thus, the Y tab includes the accumulated number of transitions for each of the 512 different Y lines being scanned by the scanner mechanism 200. The X TAB memory location includes the Pixel at which a transition is made by an X address and the type of transition. By using both the information and the X tab and Y tab direct access memory units, a profile of the leaf is stored for processing by an appropriate software arrangement for locating profile 30 within locations of the leaf L where there are no defects. The general outline of the memory data in the Y tab and X tab storage units or memories are schematically set forth in FIGS. 19, 20, respectively.

PREFERRED DATA PROCESSING CONCEPTS
(FIGS. 21-26)

Figure 21:
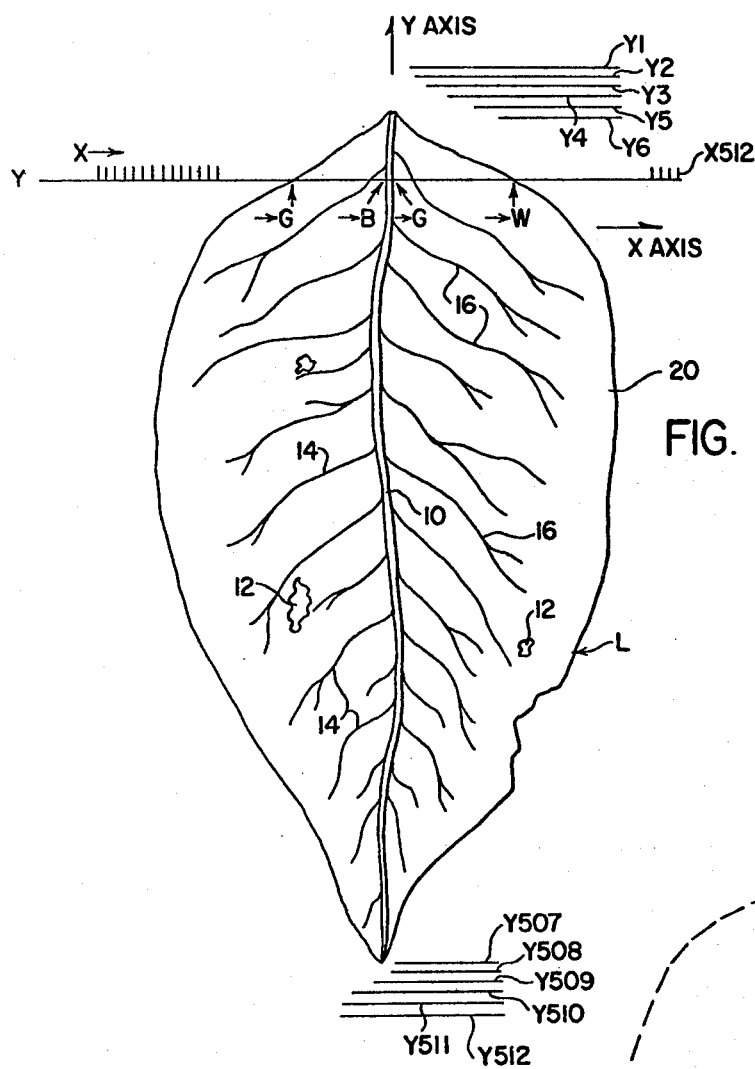
FIG. 21 is a schematic view illustrating a natural tobacco leaf and certain scanning concepts employed in the preferred scanning concept of the system.
Figure 22:
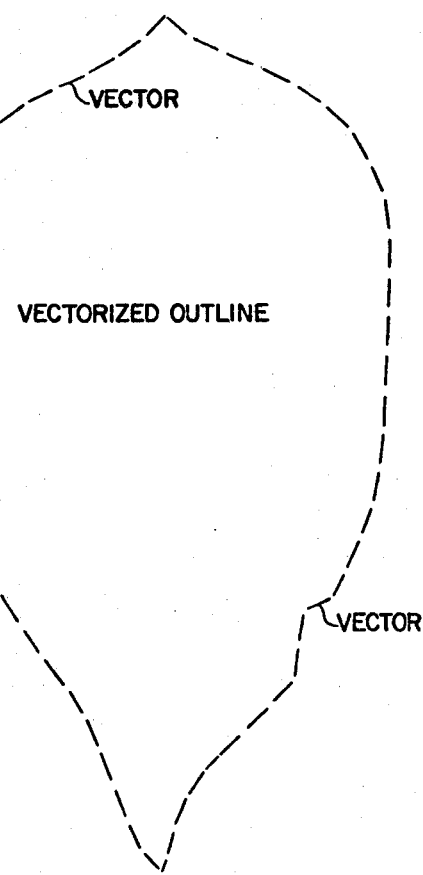
FIG. 22 is a vectorized outline of the natural leaf shown in FIG. 21 as employed in the preferred processing concept of the system.

As previously explained, the raw data or transition data, in the preferred system, is transferred to the memory 200 for use by the digital computer 240. The units 600, 602 of the preferred example correspond to memory 200 of the control diagram of FIG. 5. The computer then creates the cut locations and computes the cut coordinates for the various wrapper cuts to be made from leaf L. This can be done by a variety of software packages; however, in accordance with the present system certain concepts have been developed for use in reducing the computer time and the software complexity. These basic concepts are set forth in FIGS. 21-26. Referring now to FIG. 21, leaf L is shown with the X and Y coordinates of the scanning grid. In the single illustrated line X, it is noted that there is a transition to gray at the leaf edge, a transition to black at stem 10, a transition to gray after the stem and then a transition to white at the opposite leaf edge. This type of pattern continues through the total X sweep. Other transitions are also experienced. After the leaf has been passed, the subsequent X sweeps do not provide further transitions. At the first X sweep, there is usually no transition. Thus, the Y tab storage as shown in FIG. 19 can indicate the length of the leaf. Also, the Y tab can locate the X transitions for a given Y scan by pointing to a required X tab location. For instance, if the sixth Y line is being read, the Y tab indicates that the X sweep is between the 8th and 16th transition of the X tab. The X tab is scanned between the 8th transition and the 16th transition to give the X sweep for the sixth Y line. If the 11th Y line is to be analyzed, the X tab between the 50th and 58th transition provides the X sweep profile. This concept provides an easy access to the X sweep profile for processing by the computer by using transitions and accumulated transitions for locating information in the X tab. There is no need for a Y tab address although it is available, since the Y tabs are serially stored data between 0-512. By taking this information, in accordance with the preferred data processing system, a vector of the leaf outline shown in FIG. 22 is created by analytical geometry. This outlining vector concept provides two X coordinates at a given Y line. The first X coordinate is a first transition from white and the second Y coordinate is a last transition to white. Thereafter, the Y line is indexed a set number, such as 20-40 lines. The next Y line gives two additional outline X coordinates. These X coordinates are then noted and a mathematical vector is created in the computer for comparing cut profile 30 (in vector form) with the vectorized leaf outline to prevent interference with the leaf edge.

Figure 23:
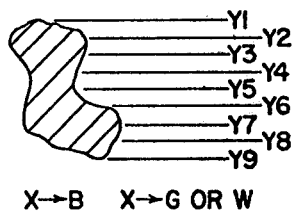
FIGS. 23, 24 and 25 illustrate further concepts used in processing data employed in the preferred system.
Figure 24:
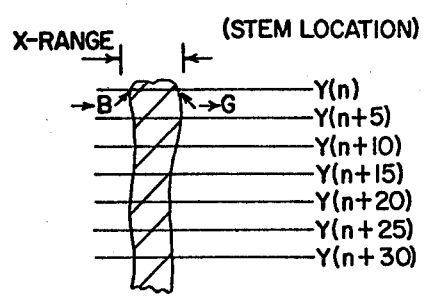

A dark area is located and recorded as shown in FIG. 23. Each of the Y lines is scanned for a transition to black and then for a transition to gray or white. This indicates a black area on the leaf at each of the Y lines. To locate holes in the leaf, each of the Y lines is scanned for a transition to white and then to gray or black. For each hole, a maximum and minimum X and a maximum and minimum Y is recorded in the memory profile to outline a hole area or domain which is rectangular and is to be avoided by a cut. A stem is located by noting a series of transitions to black and then to gray along the stem. If these transitions are aligned in the X direction for a successive number of X positions, such as 5-10 lines, it is noted that the stem has been located for storing in a memory unit of the computer. If the transitions do not align in the X direction over successive Y lines, the transitions are not the stem 10 and are known to be either the diagonal veins or dark locations previously recorded. By vectorizing the outline of the leaf, constructing a rectangle or domain around the holes, noting the black or dark locations and locating the stem, there is sufficient processed information to locate the coordinates of a cut for a wrapper to avoid the stem, dark areas, white areas and holes, as well as the outline of the leaf. FIGS. 22-25 disclose concepts used to facilitate the creation of a total leaf facsimile in X and Y coordinates and vectors therebetween for location of proper cut positions. These are novel processing concepts and are not mathematical in nature.

In FIG. 26, the general programming approach to the preferred embodiment of the invention is illustrated. Basically these program steps which could be set forth in block diagrams are self-explanatory in nature when considering FIGS. 19-25 and can be accomplished by various software routines and techniques. The concepts of FIGS. 19-25 are novel procedures which can be performed by software and used in the general program of FIG. 26.

Figure 25:
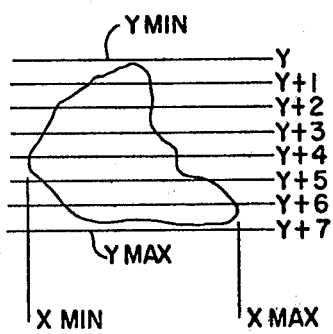

In the general program outline, after the X and Y tab have been stored in memory, steps (2)-(6) create the vector outline of the leaf as shown in FIG. 22. Steps (7)-(9) provide the hole domain as shown in FIG. 25. Steps (10) and (11) construct the stem for the leaf which is to be avoided in the cut position. By an optimizing subroutine, a safe line is constructed adjacent both sides of the stem as shown in step (12) which safe line is to be avoided in positioning a cut profile 30. In step (13), the vectorized profile 30 is mathematically positioned at one end of the leaf and adjacent the stem safe line. In step (15), if there is an intersection of the edge vector as tested in step (14), the cut profile is shifted along the safe line a given amount and step (14) is repeated. If the outline is avoided as indicated in step (16), the existence of holes or other unwanted defects is determined. If there are holes or other defects not wanted in the profile 30, it is then shifted in the Y direction along the safe line adjacent the stem as in step (17) until a position is located wherein there is no hole location or leaf outline intersection. At that time, as indicated in step (18), the black area and any minute holes in the tuck or head are tested as indicated in step (18). As indicated in step (19), if the tuckor head has black areas or other small defects the shifting process continues until the cut profile vectors reach the opposite leaf vector outline or a cut location has been determined. If the outline has been reached without a cut location, a new safe line is constructed as indicated in step (20) which is offset (in the X direction) and spaced from the previous safe line. The process is repeated until whole leaf half has been exhausted as indicated in step (21) or a cut location has been obtained. If the cut location has been obtained and meets the parameters previously discussed, the X and Y position of a point on the profile 30 and the angle of this line with respect to the Y axis is recorded and the necessary X1, X2 and Y coordinates are calculated and stored for subsequent outputting to the programmable controller to use for subsequent cutting. The angle $\phi$ occurs because the stem may not be aligned in a Y line which will give an angled safe line. This angle is small since the leaf L is aligned as best shown in FIG. 21 with the stem as vertical as practical. The type of coordinates which are required are correlated with the type of movement mechanism being used for the cutting device so that the mathematics for creating coordinates will create an output that controls the position of the cutting in accordance with the selected cut position originally identified as X, Y and $\phi$. In other words, the X1, X2 and Y coordinates are calculated from the X, Y and $\phi$ coordinates to correspond with the exact type of cutting mechanism used to adjust the leaf supporting surface or cutting surface with respect to the cutter as will be explained later. This mathematical relationship is easily programmed into the computer. This function is steps (22) and (23). After a cut position has been located, as indicated in step (24), the vectors used in the profile 30 are added to the outline vectors of the leaf to change the profile of the leaf vectors by excluding from future consideration the previously selected cutting position. Thereafter, as indicated by step (25), the process from step (13) is repeated to locate a next cut or cuts on the half of the leaf being so far processed. After all the cuts have been located on one half of the leaf, the steps commencing at step (12) are repeated for the second half of the leaf. Thereafter, the program has been completed and the computer will create a ready or access signal as indicated by step (27). This can be an output flip-flop or other arrangement to indicate to the programmable controller that the cut coordinates have been determined for a particular leaf being scanned and processed. As indicated in steps (28)–(30), the computer then waits until the programmable controller 210 indicates that it is ready to receive the cut coordinates, the cutter and cut numbers from the digital computer for use in subsequently cutting cigar wrappers from leaf L. Of course, other programming concepts could be used in practicing the present system, but the information illustrated in FIGS. 18-26 is preferred and involves certain novel concepts which reduce the software involved, decrease the cycle time for the total software program and reduce the chances of any error in the location of the cut positions for various cigar wrappers from a given natural tobacco leaf L. Basically, the outputted coordinates X1, X2 and Y are binary words that are transferred from the digital computer to the programmable controller for controlling the cut location determined by the computer. The digital information from the computer is then used directly for the location of the cut positions in a manner to be described later.

POST SCANNING PROCESSING MACHINE COMPONENTS

(FIGS. 27-39)

Referring now again to FIG. 5, the apparatus for performing the scanning and cutting process to remove cigar wrappers from leaf L includes several machine components which are generally labeled in this control concept diagram and are shown in detail in FIGS. 27-39. Essentially, the programmable controller 210 receives coordinates X1, X2 and Y for each of several cuts to be taken from the leaf together with the proper cutter and the sequence of cuts to be made. This information is received in digital form with the three coordinates in the preferred embodiment being binary representations of translation or linear movement. Programmable controller 210 uses the binary coordinates and the digital information to control the various mechanisms including the scanning mechanism previously described to process the leaf so that the computer itself can be used primarily for determining the cut positions based upon direct stored memory information indicative of the profile or image of the leaf after scanning by mechanism 200. The machine cycles controlled by the programmable controller are in accordance with common machine control techniques; therefore, the mechanisms will be described in accordance with their structure and functions.

Scanning mechanism 200 has been previously described in connection with the structure of FIG. 7; therefore, the detail of mechanism 200 is not to be repeated. Details of the other machine components will hereinafter be set forth in an embodiment of the invention to perform the desired functions; however, it is appreciated that other embodiments could be used. In some instances, the disclosed embodiments illustrate novel features which were specifically developed for the present system and which will be the subject of certain claims on the inventive aspects of the present application.

LEAF TRANSFER MECHANISM

Figure 27:
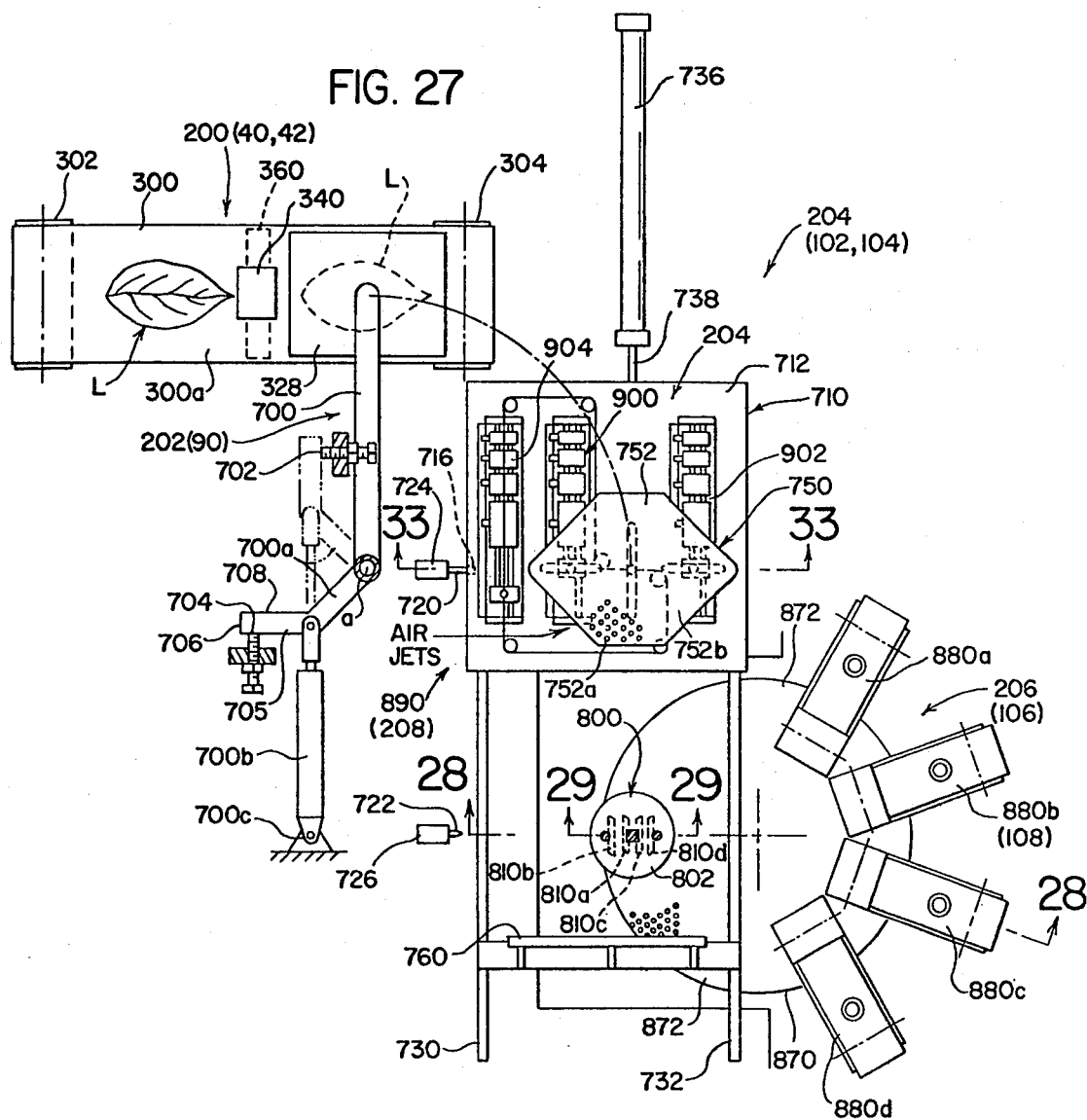
FIG. 27 is a top plan view ofan embodiment of the present invention illustrating the various structural features of a system for locating the cuts on a natural tobacco leaf, transferring the tobacco leaf to a cutting platen, cutting the cuts from the natural tobacco leaf and conveying the cuts or wrappers to a successive position for processing.

As shown in FIG. 27, the leaf is transferred from surface 300a of belt 300 by a somewhat standard vacuum type transferring arrangement which includes an arm 700 supporting a head 328 which includes a lower perforated surface generally parallel to the upwardly facing surface 300a of belt 300 in the transfer area of the scanning arrangement as shown in FIG. 7. For the purposes of simplicity in FIG. 7, arm 700 which directs either air or vacuum to head 328 is shown to be generally horizontal of belt 300; however, as shown in FIG. 27 the arm in the transfer position is essentially transverse of the belt 300. Head 328 is shifted by arm 700 between a first lead receiving position and a second leaf releasing position. Arm 700, in the illustrated embodiment, is turned by lever 700a about axis a by a cylinder 700b mounted on fixed trunnion 700c. The first leaf receiving position of arm 700 and head 328 is located by an adjustable stop 704 coacting with surface 705 of extension 706. A second adjustable stop 702 coacts with surface 708 of extension 706 to locate head 328 in the leaf releasing position. Limit switches at these stops will indicate when the transfer head 328 carried by arm 700 is in either of the two positions. Appropriate valving will direct either air or vacuum to the perforated under surface of head 328 for lifting a scanned leaf from belt 300 or depositing a leaf onto the cutting table. The belt must be in a known position with respect to the scanning operation when the leaf is removed from the belt. In this manner, the position of the leaf on the transfer head 328 is correlated and oriented to the Pixels scanned during the scanning operation. This can be done by stopping belt 300 at a fixed number of encoder pulses in line 312 after the stop scan signal in line 454 of FIG. 8. Other systems could be developed for assuring that the leaf is captured on head 328 in direct correlation to the X and Y scanning lines of the scanning operation. Irrespective of the technique used, leaf L is picked up by transfer head 328 in a fixed position with respect to the prior scanning operation which maintains the positional orientation with respect to the prior scanning of the leaf. Adjustable stop 704 allows small adjustments in the pick up position. Thereafter arm 700 is shifted by cylinder 700b against stop 702 which transfers the leaf held against the lower surface of head 328 to a fixed, known position with respect to platen 710 having an upper surface 712. Small adjustments can be made by stop 704. Leaf L is deposited onto platen 710 in a known position with respect to the prior scanning operation. Platen 710 includes lower guide wheels 714 and a side locator hole 716 into which a pin 720 or 722 is protruded by an operator, such as a solenoid 724, 726, respectively. In the leaf transfer position of platen 710, as shown in FIG. 27, pin 720 is in hole 716 so that the platen is in a fixed, known position. Transversely extending support rails 730, 732 allow movement of platen 710 by appropriate means schematically represented as cylinder 736 having a movable rod 738. Carried upon the upper portion of platen 710 is a cutting table 750 onto which the leaf is transferred when arm 700 is against stop 702. Cutting table 750 is in the oriented fixed position as shown in FIG. 27 for receiving the leaf. By coordination of the table 750 and the pick-up position of leaf L from belt 300, the leaf is deposited by transfer head 328 onto table 750 in a coordinated, oriented position with respect to its previous scanned position. The table 750 is supported on platen 710 which is held in the leaf receiving position by pin 720 entering guide slot 716. The scanned leaf which produced the desired profile in a stored memory unit is transferred onto the oriented table 750 by applying a vacuum to the cutting table and pressurizing or evacuating the head 328. This is a known transfer arrangement for tobacco in the cigar making industry. As best shown in FIGS. 32-35, cutting table 750 includes an upper nylon plate 752 having a plurality of parallel arranged openings 752a which have a diameter of approximately 0.04 inches. This plate, except for holes 752a, is a cutting board produced by Boston Cutting Die Company and is formed from hard nylon with a trademark WOGULON. Upper plate 752 has an upper cutting surface 752b. A second hard nylon plate 754 is formed with a plurality of generally parallel grooves 754a that correspond with openings 752a and have a thickness of about 3/16 of an inch. Inbetween the grooves the upper and lower plates 752, 754 are secured together for cutting rigidity. Grooves 754a do not extend to the periphery of cutting table 750 and they form a plenum chamber communicated with the openings 752a to allow a vacuum from manifold 756 to be applied to all grooves 754a and thus to the openings 752a at surface 752b. Another manifold 756a may be positioned at the opposite end of grooves 754a. In the illustrated embodiment shown in FIG. 35 a vacuum is applied to manifold 756 so that a vacuum can be directed to the upper surface 752b of cutting table 750 for clamping a transferred leaf onto the upper cutting surface for performance of the cutting operation. To remove a spent leaf from the surface 752b after the cuts have been made air pressure can be directed to grooves 754a by line 758 communicated with manifold 756a. Of course, a single manifold could be used at one end of the grooves with either vacuum or air being applied selectively to the same manifold. The manifolds are positioned generally outside the cutting area of cutting board or table 750 so that the manifolds do not adversely affect the rigidity of the board or table for the cutting operation. By providing the parallel grooves to direct pressure to the surface 752b of the cutting board or table 750, the cutting table is essentially a rigid, hard nylon cutting structure. As can be seen, vacuum holds the leaf onto the cutting board in the position to which it is transferred by transfer head 328. This position is oriented and coordinated with the scanning operation so that the leaf is in the desired position for adjustment with respect to a cutting mechanism to be hereinafter explained.

CUTTING MECHANISM

Figure 29:
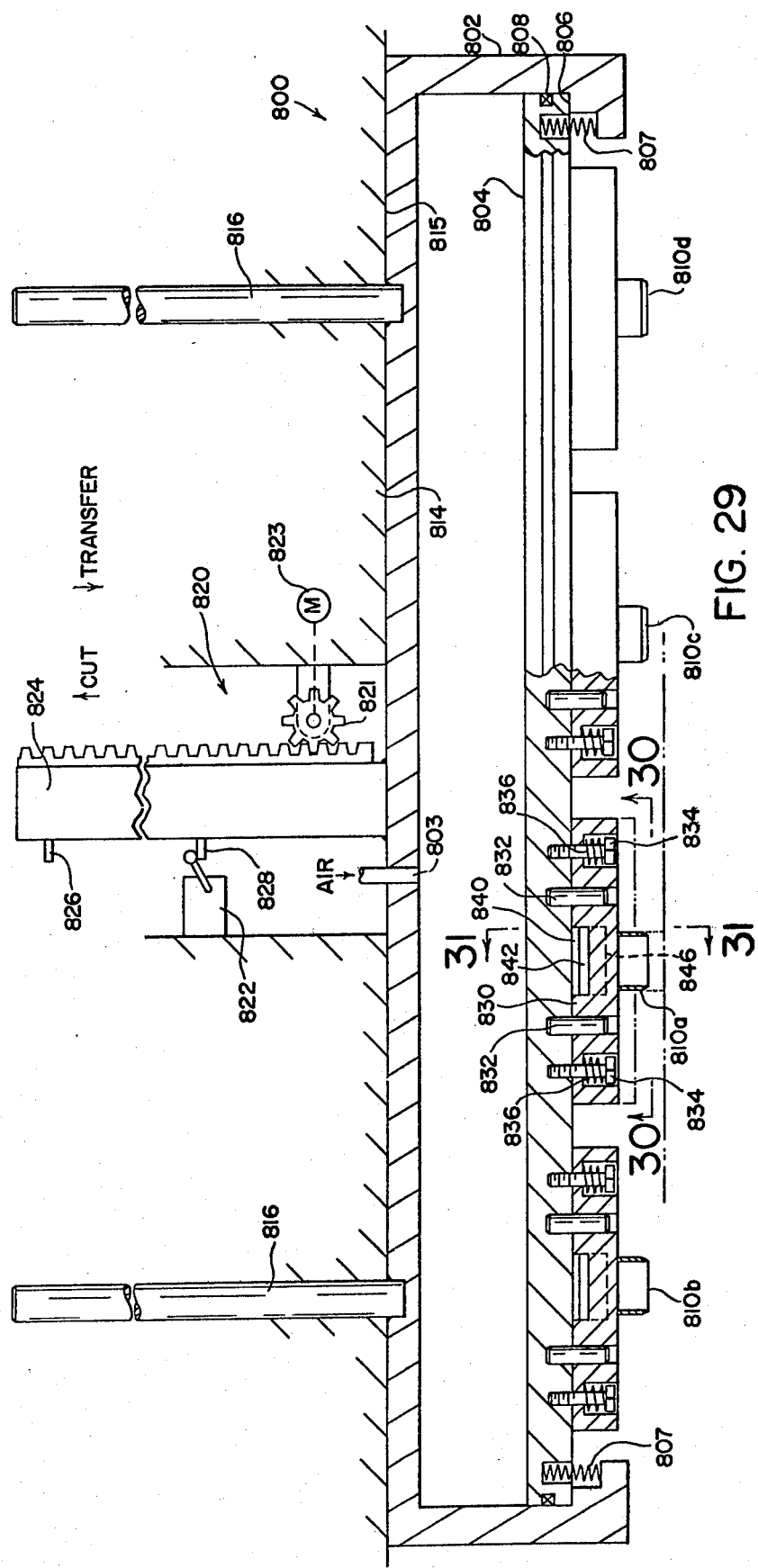
FIG. 29 is an enlarged cross-sectional view taken generally along line 29—29 of FIG. 27.
Figure 30:
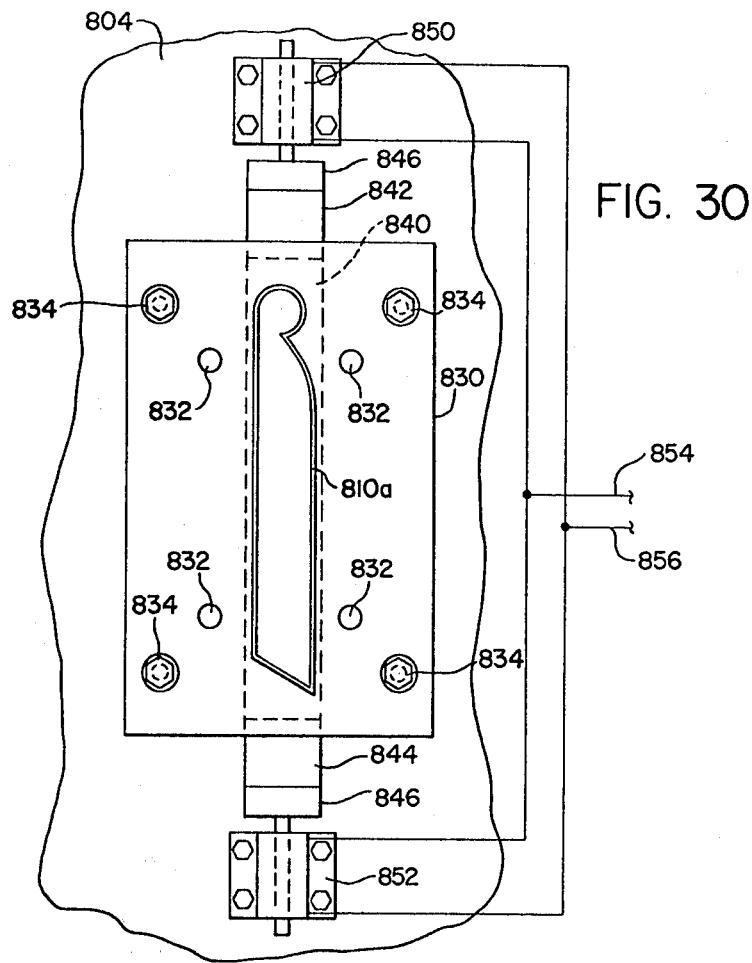
FIG. 30 is an enlarged plan view of the cutting head taken generally along line 30—30 of FIG. 29.
Figure 31:
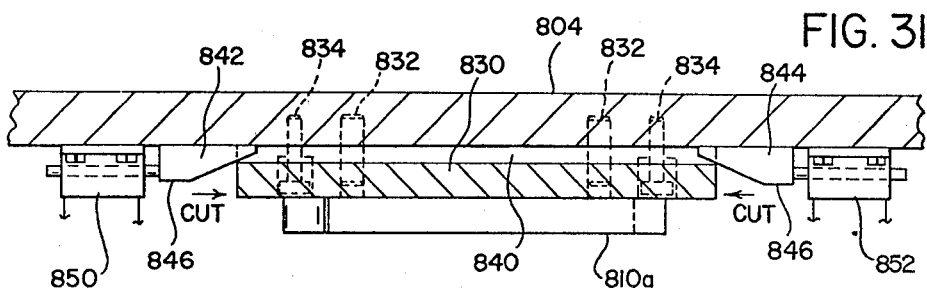
FIG. 31 is a side corss-sectional view taken generally along line 31—31 of FIG. 29.

Before describing the system for adjusting table 750 to the desired position for cutting, it is desirable to understand the preferred embodiment of the cutting mechanism 800. This mechanism is best shown in FIGS. 29-31 and includes a pancake cylinder 802 having a pneumatic inlet 803 and a piston 804 movable against a lower abutment or shoulder 806 and spring biased away from the abutment by a plurality of circumferentially spaced machine springs 807. Of course, an appropriate seal 808 is employed to seal the cylinder and piston. As illustrated, four separate cookie cutter type dies 810a-d are provided on piston 804. In practice, it is conceivable that only a left hand and right hand cutting die will be used. By showing four separate cutting dies, the system can cut two separate sized wrappers from each half of the leaf by an appropriate signal from the computer to the controller. This is useful when a large wrapper is being cut from the natural tobacco leaf and it is found that a smaller wrapper could be cut from available non-defected areas instead of one or more larger wrappers. The use of more cutting dies would increase the productivity; however, it is not necessary for the general understanding of the system. Basically, the computer commands the programmable controller 210 where to cut and which cutter 810a-d to use. Normally, the cutters 810a and 810c would be used to produce wrappers having the same general shape, but cut from opposite sides of the leaf so that they would be opposite profiled wrappers for use in different cigar making machines. The cutters themselves are fixed in position and the table 750 adjusts the tobacco leaf carried thereon to the proper cutting position. In the illustrated system, cylinder 802 is mounted on a fixed machine frame 814 having a lower abutment surface 815. A plurality of slidable guide pins 816 allow reciprocal movement of cylinder 802. A mechanism 820 is provided for shifting cylinder 802 between the upper cutting position with the cylinder against surface 815 and a lower position for transferring the cut wrapper to a subsequent apparatus for storage and use. Mechanism 820 could take a variety of forms; however, in the illustrated embodiment this mechanism includes a limit switch 822 to control the vertical position of cylinder 802. A pinion 821 driven by an appropriate motor 823 coacts with rack 824 secured on cylinder 802 to drive the cylinder between the upper cutting position and lower transfer position. The basic location of these two vertical positions is generally controlled by an appropriate mechanism, such as cams 826, 828 coacting with limit switch 822. During the cutting operation, cylinder 802 is abutting against surface 815 to rigidify the cylinder. During the wrapper transfer operation, rack 824 shifts cylinder 802 downwardly.

Cutters 810a–810d are located on piston 804 and are essentially the same in structure, except the size and/or shape of the cutters are somewhat different to create wrappers having the desired shape. It is appreciated that any number of cutters could be mounted on the piston and can be selectable for the actual cutting operation. Since each of the cutters, except for shape, is the same, only cutter 810a will be described in detail. This description will apply equally to the other cutters mounted on the piston. Indeed, only one cutter may be provided in some instances. Cutter 810a is fixed to a cutter block or support block 830 slidably received upon a plurality of dowl pins 832. Appropriately spaced machine bolts 834 include machine springs 836 which hold block 830 rigidly against the undersurface of piston 804. A slot 840 extends across the back surface of block 830 in a position generally parallel to the wrapper cutter 810a. Opposed cams 842, 844 having a cut supporting upper surface 846 are movable by solenoids 850, 852 under the control of a signal received by lines 854, 856. If a particular cutter is selected to make the cut being processed by the mechanism as shown in FIG. 27, solenoids 850, 852 shift cams 842, 844 inwardly until surfaces 846 project block 830 outwardly on dowl pins 832. In this fashion, surfaces 846 support cutter 810a in a downwardly extended active position with respect to all other cutters which remain in a retracted inactive position. Thus, only cutter 810a will cut when piston 804 is forced downwardly by pressure from inlet 803 against the action of machine springs 807. The particular signal indicating the cutter to be used controls the signal within lines 854, 856 to select any one of the cutters supported on piston 804. When piston 804 is forced downwardly against table 750, the extended cutter cuts according to the adjusted position of the table with respect to that activated cutter. As the piston 804 is retracted by exhausting air from line 803, the cigar wrapper cut by cutter 810a is held within the cutter and pulled from the surface of leaf L. To assist in this action, a vacuum, from a source not shown, may be directed to the inside or the interior of the cutter. With the wrapper cut and within the cutter, cylinder 802 can be shifted downwardly after platen 710 is retracted from the cutting position. The wrapper is now ready to be transferred for subsequent processing.

TRANSFER OF CUT WRAPPER

Figure 28:
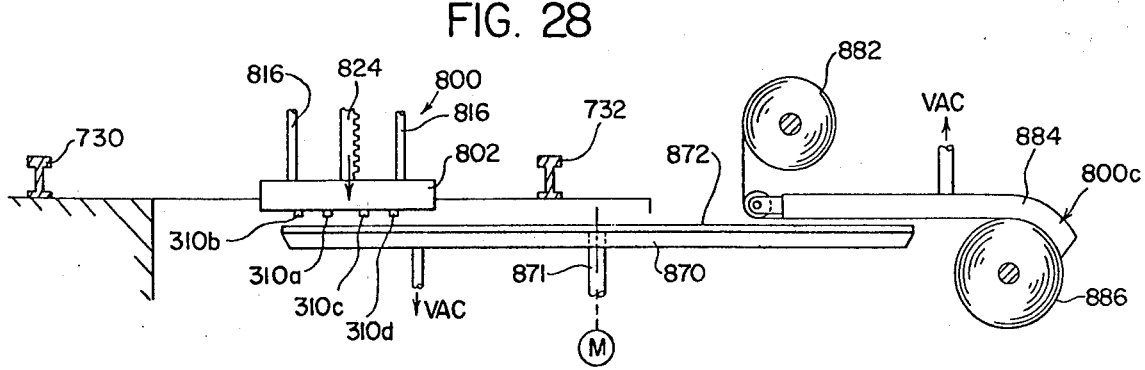
FIG. 28 is a schematic view taken generally along lines 28—28 of FIG. 27.

Referring now to FIGS. 27, 28 and 32, a cut wrapper is transferred to the vacuum table 870 indexable about center shaft 871. The upper surface 872 of the table is perforated at least in selected areas. A plenum chamber below surface 872 can apply a vacuum to the surface in accordance with standard practice. Of course, certain areas of the plenum could be formed to create surface vacuum, air pressure or atmospheric pressure to assist in wrapper transfer. When cylinder 802 is moved downwardly by rack 824, cutter 810a having a cut wrapper therein is positioned onto surface 872. Thereafter, air pressure can be applied to the cutter profile or the vacuum itself in the table 870 can draw the cut wrapper from the cutter onto surface 872. Cylinder 802 is then retracted upwardly for the next cutting cycle and table 870 is rotated or indexed to one of the standard wrapper storage bobbins 880a–880d. Each of the bobbins receives a cut wrapper from only one of the cutters 810a–810d. The standard wrapper storage bobbins 880a–880d each includes a porous belt 882 on a storage reel, a vacuum transfer and holding housing 884 and a storage bobbin 886, as shown in FIG. 28. After a wrapper cut has been made, the wrapper is deposited onto table 870 which is indexed to the desired position where a vacuum is applied to belt 882 at least adjacent the inlet end of housing 884. The cut wrapper is transferred to belt 882 and held onto the belt until it is reeled onto bobbin 886. During the indexing of table 870 and storage of a cut wrapper the next cutting operation is being performed by mechanism 204.

This wrapper removal procedure follows each cut and is repeated until all cuts are made in leaf L. The wrappers are all stored on the appropriate bobbins 880a–880d. Platen 710 carries table or cutting board 750 back to the leaf receiving position shown in FIG. 27 where the table 750 is pressurized by line 758 and air jets 890 blow the cut leaf off the table into an appropriate repository. This removing mechanism using jets 890 is schematically illustrated as block 208 in FIG. 5.

CUT LOCATING MECHANISM

Figure 36:
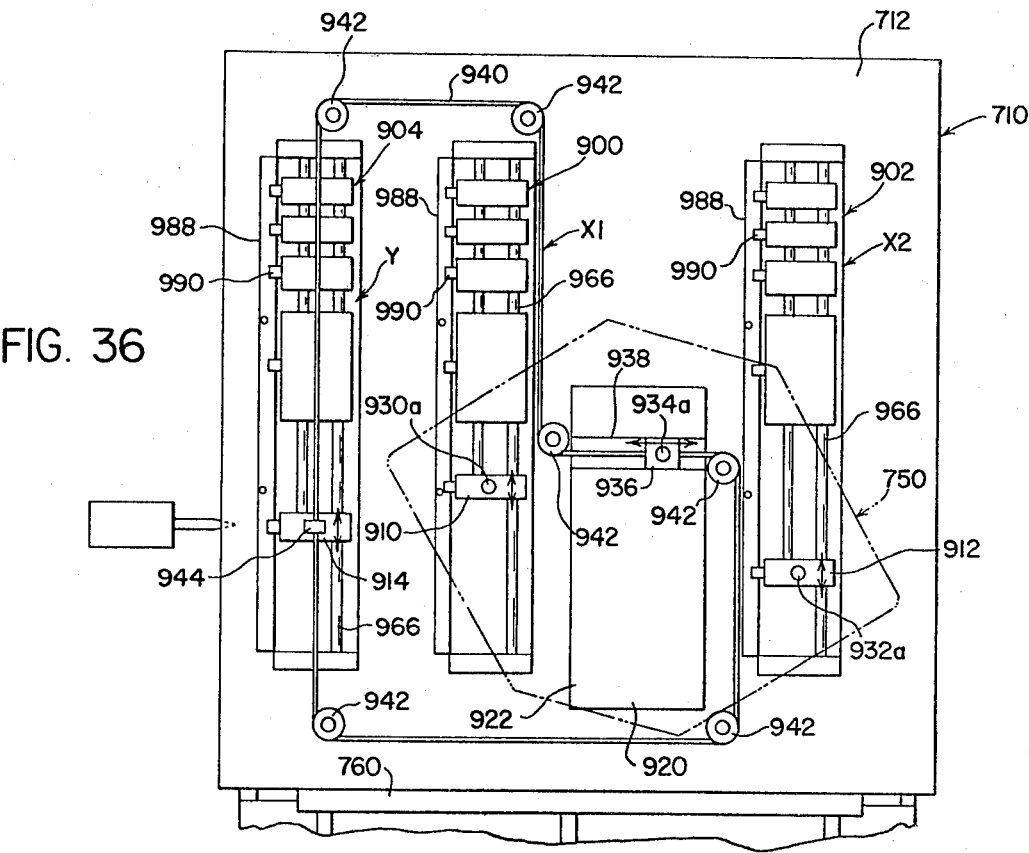
FIG. 36 is a top plan view showing in more detail the cutting platen and cutting table employed in the preferred embodiment of the present invention.
Figure 36A:
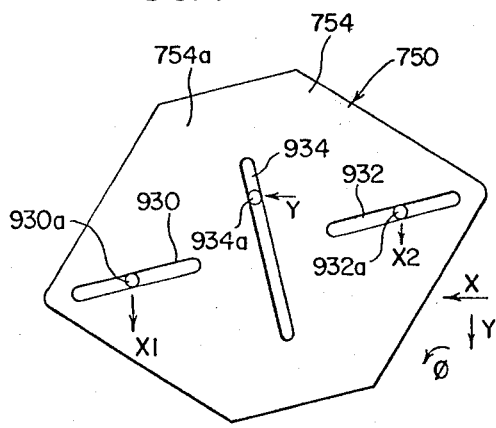
FIGS. 36A, 36B are plan views illustrating the operating characteristics of the structure shown in FIG. 36.
Figure 36B:
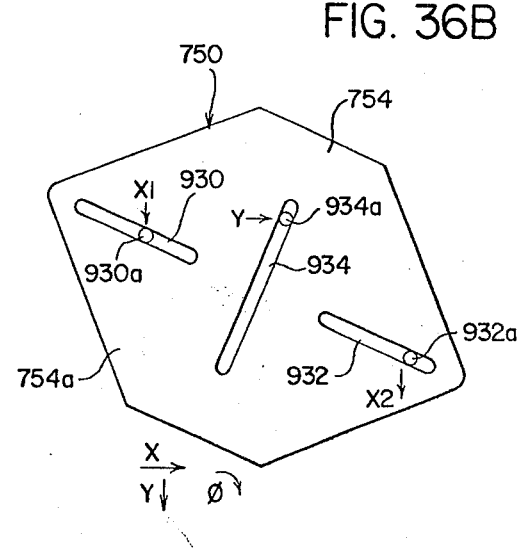

After the cut positions have been located and identified as three digital words (X1, X2, Y), these words or coordinates are used to locate the cut positions of cutting board or table 750. To perform the movement of table 750 to the various cut positions platen 710 carries table 750 to the position shown in FIG. 32. During movement of the platen to the cutting position, or after the movement has been completed, table 750 is shifted, rotated and otherwise moved to align leaf L directly below the selected cutter, which for illustrative purposes has been indicated to be wrapper cutter 810a, in the cut position identified by coordinates X1, X2 and Y. This shifting of table 750 is done by converting the three digital words (X1, X2, Y) corresponding to the proper cut position into three coplanar translation movements of the table 750 which duplicate the X, Y and $\phi$ cut position previously described. In accordance with a novel aspect of the present system, the three linear movements, which could be coordinates X, Y and $\phi$ as shown in FIGS. 36A, 36B, are obtained by linear translation distances determined by the binary number of the three separate words X1, X2 and Y. Of course, according to the type of moving mechanism used for table 750, the translation magnitude words will vary. The translation distances cause table 750 to move so that the located X, Y, $\phi$ position of leaf L is aligned with the selected cutter. In accordance with this aspect of the system, no rotary movement is required for table 750. The angular movement corresponding to $\phi$ is obtained by differential linear translation movements of two linear motors 900 and 902 fixed on surface 712 of platen 710. The details of these motors will be explained in connection with FIGS. 37–39. The motors 900, 902 and 904 each carry a movable element 910, 912, 914, respectively, which are translated a distance controlled by the binary magnitude of digital words X1, X2 and Y, respectively. These words are directly correlated with the movement of elements 910-914 to locate table 750 in the cut position as determined by the scanning and selecting process previously described. The location of table 750, in turn orients leaf L carried in a known relation on surface 752b. Of course, various systems could be used for movement of table 750, some of which would include a rotary action. It has been found that by using the translation action developed in accordance with the present system, the difficulties encountered in rotating table 750 through an angle determined by a cut coordinate is avoided. As previously discussed, the cut position can be at an angle with the Y axis since the stem of the leaf may be at an angle or the leaf may be positioned on belt 300 at a slight angle. For that reason, the preferred system requires a certain amount of angular movement which is obtained by differential translation of the two sides of table 750 by motors 900, 902.

The lower surface 754b of the lower nylon plate 754 forming table 750 rides along and is supported by an anvil 920 having an upper table support surface 922 which is parallel to lower surface 754a. Anvil 920 supports table 750 during the shifting action to locate the various cut positions. To move table 750 into the cutting positions there are provided two generally parallel slots 930, 932, as best shown in FIGS. 34, 36A and 36B. These slots are milled or otherwise provided in the lower nylon plate 754 of table 750 and are generally parallel in relationship and extend in the X direction of table 750. Between these two slots there is provided a generally orthogonal slot 934 which is at an oblique angle with slots 930, 932 which angle, in practice, is 90° so that it is aligned with the Y axis of table 750. The X and Y axes of table 750 define a grid corresponding to the scanned grid of the leaf. Of course, the grids are not marked on the scan surface or table since they are correlated by the transfer of leaf L. Pins 930a, 932a, and 934a are slidably received within slots 930, 932, and 934, respectively, so that movement of the pins in a direction generally transverse to the slots will orient table 750 for proper positioning of leaf L at the proper cutting position with respect to the selected cutter, illustrated as cutter 810a. Pins 930a, 932a move in straight lines on platen 710 which lines are parallel to the Y direction of table 750 when the table is in the leaf receiving position shown in FIGS. 27 and 34. Pin 934a is movable in a straight line on platen 710, which straight line is parallel to the X direction of table 750 when the table is in the leaf receiving position shown in FIGS. 27 and 34. In the illustrated embodiment, as best shown in FIG. 34, slots 930, 932 are aligned and on opposite sides of slot 934 and pins 930a, 932a and 934a are all aligned in a direction corresponding to the X direction of table 750 when the table 750 is in its leaf receiving position shown in FIGS. 27 and 34. Pins 930a, 932a are directly supported upon the movable elements 910, 912, respectively, of motors 900, 902, respectively. Consequently, reciprocation of elements 910, 912 causes reciprocation of pins 930a, 932a to reciprocate table 750 in the directions indicated by the arrows in FIG. 34. Pin 934a is carried by a block 936 slidably received within slot 938 of anvil 920. A drive cable 940 with a series of pulleys 942 connect block 936 drivingly with an anchor block 944 supported on element 914 which is reciprocated by the third translating motor 904. Slot 938 is orthogonal to the rest position of slot 934 and parallel to the direction of slots 930, 932. Thus, translation of element 914 causes pin 934a to move in the direction indicated in FIG. 34 a distance equal to the translation distance of element 914.

As three digital words are received, they indicate in binary language the amount of translation of the elements 910, 912, 914. The words actually provide the translated position of elements 910-914 for the cut position. If the motors 900-904 start from a zero position, the actual word gives the amount of translation. If the elements are in an intermediate position the words indicate the corrective amount of translation. Motors 900-904 may be at a prior cut position and they need not retract to the zero position to go to the next cut position. In practice, table 750 is in the zero positions of X1, X2 and the middle position of Y when in the cut receiving position shown in FIGS. 27 and 34. The binary words X1, X2 and Y are converted into movement of table 750 by the coaction between slots 930-934 and pins 930a-934a. In FIG. 34, table 750 is in the rest or leaf receiving position, which is the position used in accepting a leaf when platen 710 is in the leaf receiving position shown in FIG. 27. After the leaf has been received and vacuum has been applied through line 757 of table 750, the leaf is held in place and the programmable controller receives cut coordinates X1, X2 and Y which control the translation position of elements 910-914 controlled by motors 900-904, respectively. In this manner, the table 750 carrying the leaf is adjusted with respect to the cutter 810a, which cutter is then forced downwardly against table 750. When this happens, the upper surface 922 of anvil 920 supports the table to create a reactive force against the table to facilitate the cutting action. Thus, the movement of the cutting board or table 750 into the proper cut position is by the movement of three pins which are translated, but do not support the table in a vertical direction. The actual cutting force is against anvil 920 with upper portion 752 of table 750 being the actual cutting member. In this manner, table 750 has a low weight and develops low inertia forces. Pins 930a-934a need not have a heavy construction to withstand the subsequent cutting forces. Thus, the pins develop low inertia forces. In practice, a head is provided on the moving pins 930a, 932a to coact with a retaining structure adjacent slots 930,932 to hold table 750 in the horizontal position as it is shifted. As previously mentioned, after the cut has been made the wrapper is removed by the cutter and platen 710 moves to a position clearing cylinder 802 so that the cylinder can be moved downwardly to transfer the cut wrapper onto vacuum table 870 for subsequent indexing to one of the wrapper bobbins 880a-880d. When the cut is made by cutter 810a, table 870 is indexed to wrapper storage mechanism 880a where the cut wrapper is transferred to storage element or bobbin 886 for subsequent loading into a cigar machine in accordance with standard cigar making practice. As shown in FIG. 37, the top of the pins 930a,932a can include a head 950 held within the respective slots by an appropriate plate 952. Other arrangements, such as a T-slot and head, could be used to hold table 750 onto the moving pins for movement therewith. The actual cutting action takes place against the upper surface 922 of anvil 920.

FIG. 36A shows an example where table 750 has been shifted to a cut position with X1 greater than X2 and Y shifted to the left, as viewed from surface 754a. Another example is shown in FIG. 36B with X2 greater than X1 and Y shifted to the right as viewed from the under surface 754a.

A variety of structures could be used to translate elements 910-914 in a manner controlled by digital signals; however, one mechanism for accomplishing the conversion between digital coordinates in binary words and translation of the movement elements is a binary motor concept. This concept is used in motors 900-904. Since each of these motors is essentially the same, only motor 900 will be described in detail and this description will apply equally to binary motors 902 and 904. As shown in FIGS. 37-38, motor 900 includes a series of cylinders 960-1 to 960-8 having internal double acting pistons 962-1 to 962-8. These cylinders are connected together so that an eight bit binary word used to control the pressure in each of the cylinders will translate element 910 a distance corresponding to the numerical value of the binary number. Of course, the binary number could include various number of bits. A variety of structures could be used for interconnecting the pistons and cylinders; however, in the illustrated embodiment the cylinders are connected together in the following sets: 960-1 and 960-2, 960-3 and 960-4, 960-5 and 960-6, and 960-7 and 960-8. Piston 962-1 is fixed at one end of motor frame 963. The pistons are interconnected in the following sets: 962-2 and 962-3, 962-4 and 962-5; 962-6 and 962-7. Piston 962-8 is connected to the movable element 910 by shaft 964. Successive pistons have strokes which vary in binary fashion, i.e. vary as a factor of 2. In the illustrated embodiment as set forth graphically in FIG. 39, the first cylinder has a stroke of 0.04 inches. Each of the successive cylinders has strokes which are factors of 2 of this stroke. A support and bearing rod 966 extends the complete length of motor frame 963 and passes though the respective cylinders as shown in cross-section in FIG. 38. This rod allows translation of the various cylinders in a direction parallel to the stroke of the pistons within the cylinders. To support the other side of the cylinders, there is provided a fixed rail 988 supported on a fixed stand 989. The cylinder housing includes upper and lower guide plates 990, 992 which slide along the fixed rail 988 to support the cylinder housings in the vertical direction. Rod 966 controls the horizontal movement of the motor. To move the pistons in the respective cylinders, there is provided a double acting valving unit 970 including valves 965-1 to 965-8 schematically shown in FIG. 39. These valves are controlled by the binary logic on bit No. 1 to bit No. 8 of the binary word indicating the amount of translation for element 910. Flexible conduits 972 are the ON or the YES fluid conduits, whereas the flexible conduits or couplings 974 are the OFF or NO conduits. A selected binary word indicating the movement of element 910 controls the valves shown in FIG. 39 to control fluid pressure to the various cylinders shown in FIG. 37. By the illustrated example, the amount of movement of element 910 corresponds to the magnitude of the binary number in the 8 bit word directed to the valving unit 970. Element 910 is translated in accordance with the binary word used as one coordinate (X1) in locating the cut position of table 750 with respect to cutter 810a. The operation of the three motors 900-904 (X1, X2 and Y) duplicates the located cut position provided as three binary words (8 bits). The three motors are moved in accordance with the relationship of the pins and grooves needed to locate the upper surface of table 750 for cutting. Primarily, the cut locating mechanism involves three translating devices which are translated in accordance with the desired ultimate position of leaf L, as indicated by binary numbers or digital information.

CONCEPTUAL AND APPARATUS MODIFICATIONS AND ILLUSTRATIONS (FIGURES 40, 40A AND 41-43)

Figure 40:
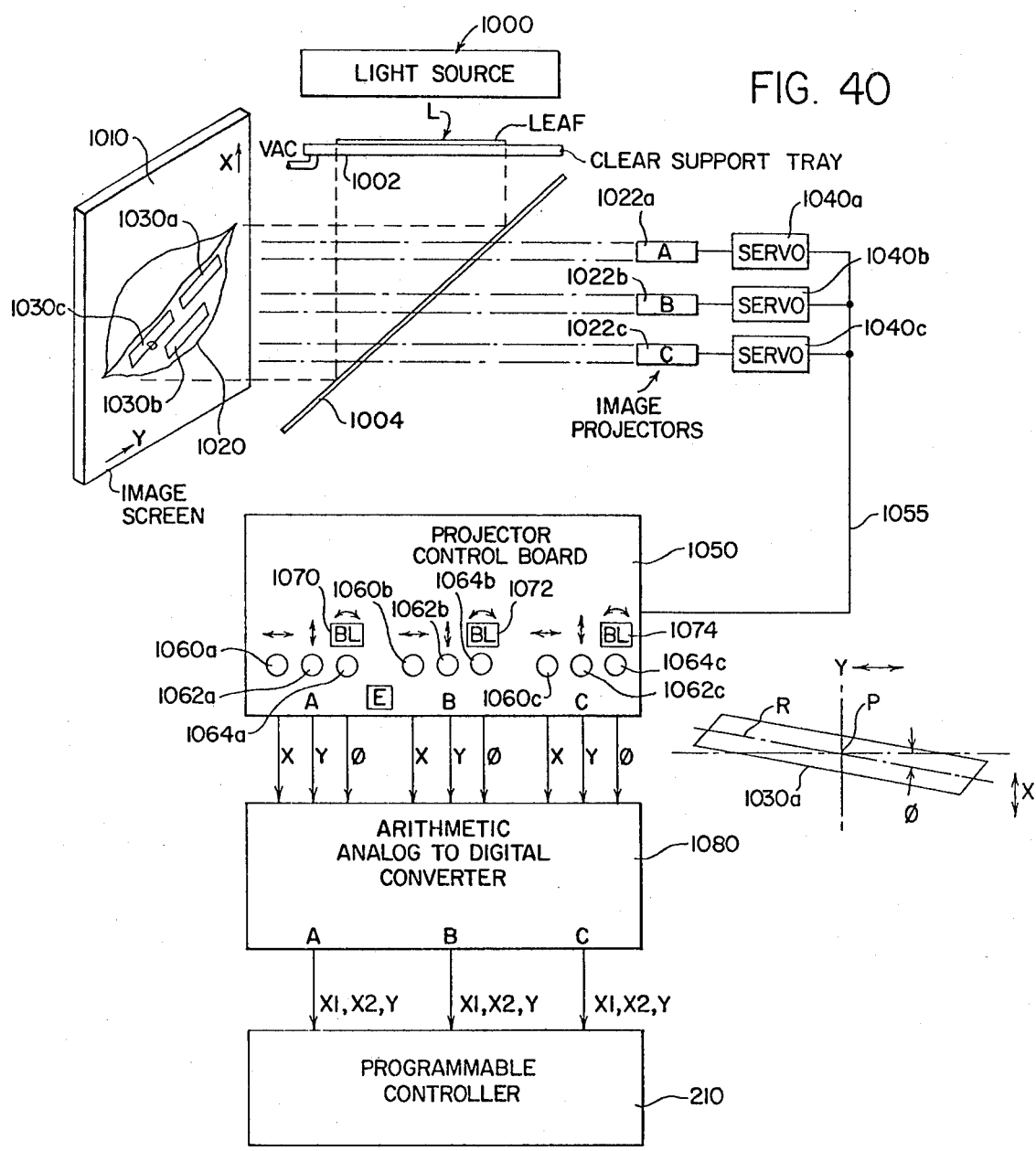
FIG. 40 is a schematic view of a modification of the illustrated preferred system showing certain features of the present invention.
Figure 40A:
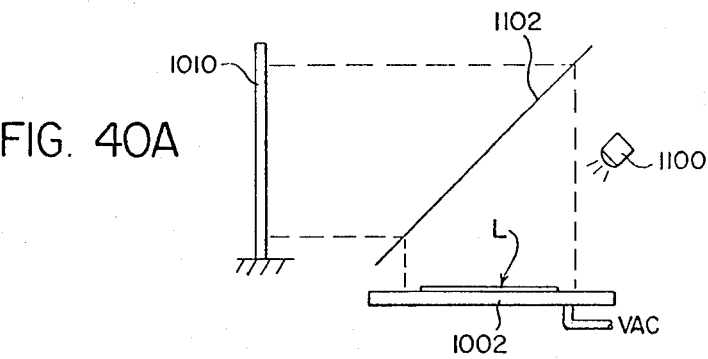
FIG. 40A is a schematic view showing a modified portion of the structure as illustrated in FIG. 40.

Referring now to FIG. 40, a conceptual variation of the system as so far described is illustrated. In this conceptual concept, an appropriate light 1000 passes light rays through a leaf support member 1002 onto which a leaf L is supported. The support member is translucent or transparent so that light rays are transmitted through the support member to an appropriately positioned one way mirror 1004 which reflects the image of the leaf in oriented fashion onto the display screen 1010. The display image 1020 is intersected by light images from projectors 1022a, 1022b, and 1022c which project images 1030a, 1030b and 1030c corresponding to the cut profile images shown in FIG. 3 through mirror 1004 onto screen 1010. Servo mechanisms 1040a, 1040b and 1040c are controlled by a unit 1050 having three sets of manually manipulated elements 1060a-c, 1062a-c and 1064a-c. For each of the sets of elements, there is provides a blanking button 1070, 1072, 1074, respectively. Unit 1050 also has an enter data button E. In practice, elements 1060a, 1062a, and 1064a are adjusted until the image or outline 1030a is in a position avoiding all defects in the image 1020 of leaf L. This movement of elements on the face of unit 1050 controls servo mechanisms 1040a-c by an appropriate interconnect indicated as line 1055. After the first outline is properly positioned at the X, Y and $\phi$ coordinates of line R and point P thereon, the knobs for controlling the next profile 1030b are manipulated until the image is in the proper position to create corresponding X, Y and $\phi$ coordinates. Thereafter, the third image 1030c is manipulated to obtain a cut position. If a third cut can not be made in a nondefect area of the leaf image 1020, the blanking button 1074 is actuated to indicate that no cut is possible for this third image. The same type of unit 1050 may be used on the other half of the leaf image to manually manipulate the cut profiles onto the visually displayed leaf. Thereafter, the information determined by the position of the control elements on unit 1050 is transmitted as X, Y and $\phi$ to an analog to digital converter 1080. This digital information is arithmetically converted to coordinate forms acceptable by programmable controller 210 so that the data provided by converter 1080 to programmable controller 210 is the coordinates X1, X2 and Y as used in the preferred embodiment of the system as so far explained. The system shown in FIG. 40 illustrates a remotely positioned image determined by the leaf itself into which is fitted the cutting profiles. The information generated is converted to digital information which is indicative of translation that controls the operation of motors 900, 902 and 904 in the illustrated embodiment of the invention. Referring now to FIG. 40A, the system shown in FIG. 40 is modified to have a light source 1100 which shines upon leaf L and transmits the front lighted image to the screen 1010 through an optical system 1102. Otherwise, the system of FIG. 40A operates in accordance with the general system shown in FIG. 40.

Figure 41:
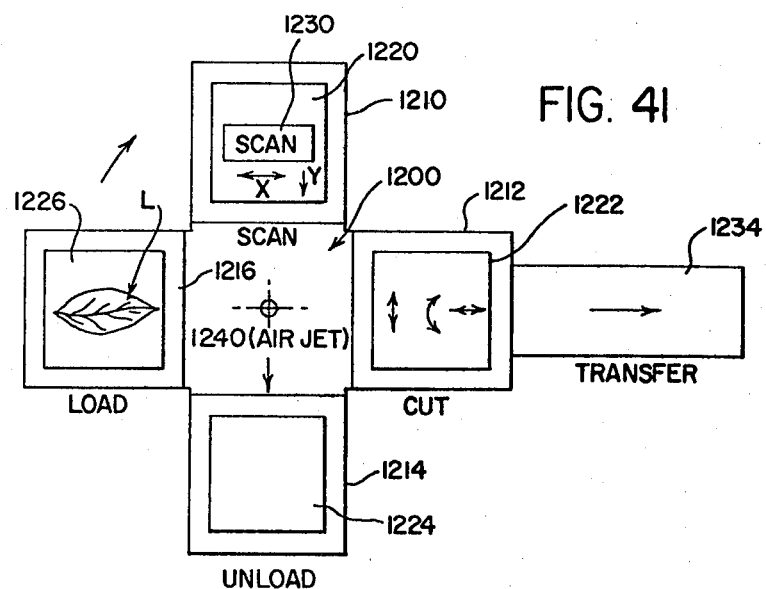
FIG. 41 is a further embodiment of the present invention wherein the scanning, cutting, loading and unloading of a natural leaf onto the cutting platen is done at angularly positioned locations and the cutting occurs on the same support structure as used during the scanning operation.
Figure 43:
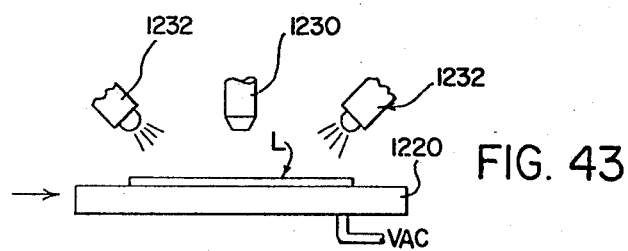

FIG. 41 schematically illustrates a modified mechanism for processing natural tobacco leaf L. This mechanism includes an indexable turret 1200 movable between scan, cut, unload and load positions and having four supporting platens 1210, 1212, 1214 and 1216. Each of these platens is similar to platen 710 and movably supports cutting boards 1220, 1222, 1224 and 1226 similar to table 750. The cutting tables each include a vacuum surface for holding leaf L onto the cutting table as previously described in the preferred system for processing the natural leaf. A scanning head 1230 is used to scan the leaf L in the X direction as the cutting table is indexed to the Y direction. As shown in FIG. 43, the leaf L can be illuminated from the front by a plurality of light sources 1232. Of course, light could be positioned under the cutting board 1220 in the scanning position. Turret 1200 is indexed to bring the scanned leaf into the cut position. At that position, the cutting table is indexed and rotated to the various cutting locations and the cutting process is performed as previously described. To transfer the wrapper to a transfer device or vacuum conveyor, platen 1212 as shown in the cutting position, can be indexed to the left to allow transfer of a cut wrapper, as previously described, onto a vacuum belt or conveyor 1234. Thereafter, turret 1200 is indexed to the unload position and air jets 1240 blow the cut leaf from cutting board 1224 as vacuum is released from the cutting table. Following this action, turret 1200 is indexed to the load position where leaf L is spread onto the cutting table 1226. Each of these processes is being performed simultaneously; therefore, during each index, each of the functions previously described is performed at the various illustrated locations. This mechanism illustrates the concept of cutting the leaf on the scanning surface. This does not require reorientation of the leaf onto a new surface as used in the preferred system.

Figure 42:
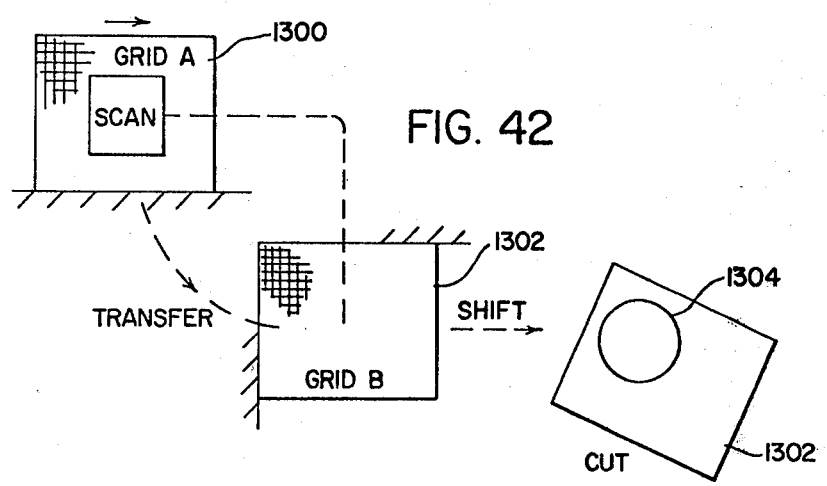
FIG. 42 is a schematic view illustrating the grid coordination concept employed in the preferred embodiment of the present invention; and, FIG. 43 is a simplified schematic view illustrating a modification of the invention as could be used in the schematic structure illustrated in FIG. 41.

Referring now to FIG. 42, a conceptual aspect of the present invention is illustrated. In this aspect, a grid A provided on a first member 1300 is fixedly positioned with a grid B on a member 1302. During the scanning operation, the light intensity of the various elements or Pixels on grid A are recorded. Thereafter, the leaf is transferred along the direction indicated by the arrow to grid B. This transfer orients the leaf onto grid B in accordance with the scanning system previously described with respect to grid A. Thus, by utilizing the scanned concept on grid A this concept applies equally to grid B onto which the leaf is oriented. Member 1302 can then be shifted with respect to cutter 1304 to cut a wrapper based upon the position of grid B whereas the scanning has been accomplished with respect to grid A. This is the concept used in the preferred system of the present invention and is shown in FIG. 42 for illustrative purposes only. Also, this new system can cut different sized wrappers wherein the prior manual system cut only a single sized wrapper from a leaf half.

Having thus defined the invention, it is claimed:

1. A device for cutting a piece from a flat workpiece at a location identified by two or more binary coded numbers, said device comprising: a cutter; a cutting platen having an upper workpiece supporting cutting surface and a lower portion; a pluarlity of upstanding shiftable members, guide means on said platen adjacent said lower portion for loosely receiving said members; means for moving said members in accordance with said coded numbers; and means for forcing said cutter against said cutting surface, said guide means including first, second and third guide ways on said platen, said first and second guide ways extending generally in a first direction and said third guide way extending in a second direction at a known angle to said first direction wherein said shiftable members are first, second and third drive elements slidably received in said first, second and third guide ways respectively and wherein said moving means includes first drive means for shifting said first drive element in a drive direction generally transverse to said first guide way, second drive means for shifting said second drive element in a drive direction generally transverse to said second guide way, and third drive means for shifting said third drive element in a drive direction generally transverse to said third guide way.

2. A device as defined in claim 1 wherein at least said first and second drive means includes a drive member movable by a binary fluid motor including a series of axially aligned fluid actuated units, each of said units including a cylinder and an extendable piston having a controlled stroke with respect to said cylinder, said respective strokes having a known binary distance relationship, means for interconnecting said fluid units of each fluid motor to cause movement of said driven member a rectilinear distance corresponding to the summation of the strokes of the extended pistons of said units of each fluid motor and means for extending said pistons of said units for each fluid motor in response to said coded numbers.

3. A device as defined in claim 2 wherein said third drive means includes a drive member movable by a third fluid motor including a series of axially aligned fluid actuated units, each of said units of said third fluid motor including a cylinder and an extendable piston having a controlled stroke with respect to said cylinder, said strokes of said units of said third fluid motor having a known binary distance relationship, means for interconnecting said fluid units of said third fluid motor to cause movement of said third driven member a rectilinear distance corresponding to the summation of the strokes of the extended pistons of said units of said third fluid motor and means for extending said pistons of said units for said third fluid motor in response to a selected coded number.

4. A device as defined in claim 3 including means for locating said third fluid motor in a selected intermediate position between cuts by said cutter.

5. A device as defined in claim 1 wherein said third drive means includes a drive member movable by a third fluid motor including a series of axially aligned fluid actuated units, each of said units of said third fluid motor including a cylinder and an extendable piston having a controlled stroke with respect to said cylinder, said strokes of said units of said third fluid motor having binary distance relationship, means for interconnecting said fluid units of said third fluid motor to cause movement of said third driven member a rectilinear distance corresponding to the summation of the strokes of the extended pistons of said units of said third fluid motor and means for extending said pistons of said units for said third fluid motor in response to a selected coded number.

6. A device as defined in claim 5 including means for locating said third fluid motor in a selected intermediate position between cuts by said cutter.

7. A device as defined in claim 2 including means for locating at least one of said drive means in an intermediate position between cuts by said cutter.

8. A device as defined in claim 1 including means for locating at least one of said drive means in an intermediate position between cuts by said cutter.

9. A device as defined in claim 1 including vacuum means for supporting said workpiece on said cutting surface.

10. A device as defined in claim 9 wherein said cutting platen includes a plenum chamber below said cutting surface, means for directing a vacuum to said plenum chamber, said chamber comprising a plurality of spaced subchambers and apertures extending between said cutting surface and one of said subchambers.

11. A device for moving a cutting platen with respect to a vertically movable cutter to a cutting position, said cutter having a preselected cutting peripheral edge, said platen having an upper generally flat cutting surface for supporting a generally flat sheet and a lower portion, said device comprising: two upstanding shiftable pin members; first and second generally parallel guide ways on said platen and adjacent to said lower portion, said guide ways being generally parallel and dimensioned to allow translation of one of said pin members in each of said guide ways; means for extending said pin members into said guide ways; means for allowing relative rotation between said pin members and said guide ways; and, first and second drive means for shifting said pin members preselected, independent distances along generally parallel paths to impart both rotation and translation to said platen.

12. A device as defined in claim 11 wherein said first and second drive means each includes a drive member movable by a fluid motor and means for moving each of said fluid motors a distance determined by a multi-bit digital signal.

13. A device as defined in claim 12 wherein said fluid motors each include a series of axially aligned fluid actuation units, each of said units including a cylinder and an extendable piston having a controlled stroke with respect to said cylinder, said respective strokes having a known binary distance relationship, means for interconnecting said fluid units of each fluid motor to cause movement of said shiftable pin members to a rectilinear position corresponding to the summation of the strokes of the extended pistons of said units of each of said fluid motors and means for extending selected ones of said pistons in response to the bits of said multi-bit digital signal.

14. A device for cutting a piece from a flat workpiece at a location identified by two or more binary coded numbers, said device comprising: a cutter having the shape of said piece; a cutting platen having an upper workpiece supporting cutting surface and a lower portion; a plurality of upstanding shiftable pin members; guide groove means having side walls and located on said platen adjacent said lower portion for receiving said pin members with said pin members being freely movable vertically with respect to said guide groove means; means for allowing relative rotation between said pin members and said guide groove means; means for moving said members in accordance with said coded numbers; and means for forcing said cutter against said cutting surface.

* * * * *

UNITED STATES PATENT AND TRADEMARK OFFICE
CERTIFICATE OF CORRECTION

PATENT NO. : 4,226,148

DATED : October 7, 1980

INVENTOR(S) : David J. Logan; Robert J. Pavone

It is certified that error appears in the above-identified patent and that said Letters Patent is hereby corrected as shown below:

In the drawings, Sheet 1, Fig. 1, the lead line from the lower left reference numeral "12" should extend to the leaf hole directly thereabove; Sheet 2, Fig. 4, in box 42 "INDENTIFIABLE" should read --IDENTIFIABLE--; Sheet 14, Fig. 28, reference numerals "310a, 310b, 310c and 310d" should read --810a, 810b, 810c and 810d--, respectively, and reference numeral "800c" should read --880c--; Sheet 17, Fig. 32, reference numeral "756" should read --752--; Fig. 35, reference numeral "756" at bottom of figure should read --934--; Sheet 18, Figs. 36A and 36B, reference numeral "754a" should read --754b--; Sheet 19, Fig. 37, reference numeral "754a" should read --754b--. Column 1, line 47, "knon" should read --known--. Column 3, line 60, after "third" insert --drive--. Column 5, line 14, "plate" should read --platen--. Column 6, line 7, after "is" insert --a--; line 15, "FIG." should read --FIGS.--; line 36, "ofan" should read --of an--. Column 8, line 18, "Th" should read --The--. Column 9, line 8, "over view" should read --overview--. Column 10, line 19, "unit" should read --until--; line 30, after "form" insert --of--. Column 11, line 2, after "by" insert --a--; line 24, after "leaf" insert --after--; line 53, "not" should read --now--; line 58, "acknowledge" should read --acknowledges--; line 63, before "the" insert --and--. Column 16, line 66, "Th" should read --The--. Column 18, line 7, "Inbetween should read --In between--. Column 19, line 49, "existance" should read --existence--. Column 21, line 10, after "surface" insert --300a--; line 67 (actual) reference numeral "202" should read --220--. Column 22, line 30, "lines" should

UNITED STATES PATENT AND TRADEMARK OFFICE
CERTIFICATE OF CORRECTION

PATENT NO. : 4,226,148            Page 2 of 2.
DATED     : October 7, 1980
INVENTOR(S) : David J. Logan; Robert J. Pavone It is certified that error appears in the above-identified patent and that said Letters Patent is hereby corrected as shown below:

read --line--; line 34 "the" (first occurrence) should read --The--. Column 23, line 4, "assessing" should read "accessing--; lines 31 and 33, reference numeral "200" should read --220--; line 32, reference numerals "600,602" should read --660,662--. Column 24, line 24, "X" should read --Y--. Column 25, line 6, "tuckor" should read --tuck or--; line 13, after "until" insert --the--. Column 26, line 60, "lead" should read --leaf--. Column 27, line 26, reference numeral "704" should read --702--; line 63, "Inbetween" should read --In between--. Column 29, lines 26 and 37, "dowl" should read --dowel--; line 32, "upper" should read --under--. Column 31, line 23, reference numeral "754a" should read --754b--. Column 32, lines 65 and 68, reference numeral "754a" should read --754b--. Column 34, lines 23-24, "provides" should read --provided--. Column 35, line 8, "to" should read --in--. Column 36, line 50 (actual), before "binary" insert --a known--.

Signed and Sealed this

Twenty-fifth Day of May, 1993

Attest:

*Attesting Officer*

MICHAEL K. KIRK

*Acting Commissioner of Patents and Trademarks*